(12) United States Patent
Kusano et al.

(10) Patent No.: US 9,403,897 B2
(45) Date of Patent: Aug. 2, 2016

(54) PROTEINACEOUS PROTEASE INHIBITOR AND PROTEIN SOLUTION AND DETERGENT COMPOSITION CONTAINING IT

(71) Applicant: Sanyo Chemical Industries, Ltd., Kyoto (JP)

(72) Inventors: Miki Kusano, Kyoto (JP); Fusamitsu Yanagihara, Kyoto (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 10 days.

(21) Appl. No.: 14/347,298

(22) PCT Filed: Oct. 5, 2012

(86) PCT No.: PCT/JP2012/076043
§ 371 (c)(1),
(2) Date: Mar. 26, 2014

(87) PCT Pub. No.: WO2013/054774
PCT Pub. Date: Apr. 18, 2013

(65) Prior Publication Data
US 2014/0357543 A1    Dec. 4, 2014

(30) Foreign Application Priority Data

Oct. 12, 2011 (JP) ................................. 2011-224880
Jan. 17, 2012 (JP) ................................. 2012-006811
Aug. 23, 2012 (JP) ................................. 2012-183932

(51) Int. Cl.
*C11D 9/00* (2006.01)
*A61K 38/48* (2006.01)
(Continued)

(52) U.S. Cl.
CPC ................ *C07K 14/81* (2013.01); *C11D 3/386* (2013.01); *C11D 3/38618* (2013.01); *C11D 3/38663* (2013.01)

(58) Field of Classification Search
None
See application file for complete search history.

(56) References Cited

U.S. PATENT DOCUMENTS 5,674,833 A    10/1997    Mikkelsen et al.
6,579,698 B1    6/2003    Correa et al.
(Continued)

FOREIGN PATENT DOCUMENTS

EP        1093518        4/2001
JP        5-507283        10/1993
(Continued)

OTHER PUBLICATIONS

International Search Report issued Nov. 20, 2012 in International (PCT) Application No. PCT/JP2012/076043.

(Continued)

*Primary Examiner* — Jeanette Lieb
(74) *Attorney, Agent, or Firm* — Wenderoth, Lind & Ponack, L.L.P.

(57) ABSTRACT

An object of the present invention is to provide proteinaceous protease inhibitors with moderate inhibitory activity. A proteinaceous protease inhibitor of the present invention includes an amino acid sequence (Y) or an amino acid sequence (Y'), the amino acid sequence (Y) being different from the amino acid sequence (A) of a proteinaceous protease inhibitor (BC), represented by SEQ ID NO:1, by one to eight amino acid replacements with amino acids different from replaced amino acids, the amino acid sequence (Y') having at least 80% homology to the amino acid sequence (Y), wherein the proteinaceous protease inhibitor satisfies at least one of the following conditions (1) to (8):

(1) the amino acid residue at a position corresponding to residue 12 of the amino acid sequence (A) in the amino acid sequence (Y) or (Y') is an amino acid (X1) defined below;

(2) the amino acid residue at a position corresponding to residue 38 of the amino acid sequence (A) in the amino acid sequence (Y) or (Y') is an amino acid (X2) defined below;

(3) the amino acid residue at a position corresponding to residue 48 of the amino acid sequence (A) in the amino acid sequence (Y) or (Y') is an amino acid (X3) defined below;

(4) the amino acid residue at a position corresponding to residue 50 of the amino acid sequence (A) in the amino acid sequence (Y) or (Y') is an amino acid (X4) defined below;

(5) the amino acid residue at a position corresponding to residue 51 of the amino acid sequence (A) in the amino acid sequence (Y) or (Y') is an amino acid (X5) defined below;

(6) the amino acid residue at a position corresponding to residue 52 of the amino acid sequence (A) in the amino acid sequence (Y) or (Y') is an amino acid (X6) defined below;

(7) the amino acid residue at a position corresponding to residue 53 of the amino acid sequence (A) in the amino acid sequence (Y) or (Y') is an amino acid (X7) defined below;

(8) the amino acid residue at a position corresponding to residue 70 of the amino acid sequence (A) in the amino acid sequence (Y) or (Y') is an amino acid (X8) defined below:

(X1): any of amino acids (X0) other than Glu
(X2): any of the amino acids (X0) other than Val and Ile
(X3): any of the amino acids (X0) other than Met
(X4): any of the amino acids (X0) other than Tyr
(X5): any of the amino acids (X0) other than Arg
(X6): any of the amino acids (X0) other than Ile
(X7): any of the amino acids (X0) other than Asp
(X8): any of the amino acids (X0) other than Arg; and
(X0): Ala, Arg, Asn, Asp, Cys, Gly, Gln, Glu, His, Ile, Leu, Lys, Met, Phe, Pro, Ser, Thr, Trp, Tyr, or Val.

22 Claims, No Drawings

(51) Int. Cl.
*C07K 14/81* (2006.01)
*C11D 3/386* (2006.01)

(56) References Cited

U.S. PATENT DOCUMENTS

2004/0038845 A1* 2/2004 Pedersen et al. ............ 510/392
2005/0010973 A1* 1/2005 Rao ...................... A23K 1/1631
  800/278

FOREIGN PATENT DOCUMENTS

| JP | 2000-506394 | 5/2000 |
| JP | 2004-500007 | 1/2004 |
| WO | 92/05239 | 4/1992 |
| WO | 93/20175 | 10/1993 |
| WO | 02/18588 | 3/2002 |

OTHER PUBLICATIONS

Poerio et al., "Primary Structure and Reactive Site of a Novel Wheat Proteinase Inhibitor of Subtilisin and Chymotrypsin", Biological Chemistry, vol. 384, Feb. 2003, pp. 295-304.
Murao et al., "S-SI, a New Alkaline Protease Inhibitor from *Streptomyces albogriseolus* S-3253", Agricultural and Biological Chemistry, vol. 36, No. 1, 1972, pp. 160-163.
McPhalen et al., "Preliminary Crystallographic Data for the Serine Protease Inhibitor CI-2 from Barley Seeds", Journal of Molecular Biology, vol. 168, 1983, pp. 445-447.
Ganz et al., "Stabilized variant of Streptomyces subtilisin inhibitor and its use in stabilizing subtilisin BPN", Protein Engineering, Design & Selection, vol. 17, No. 4, pp. 333-339, 2004.

* cited by examiner

```
                         SEQUENCE LISTING

<160> NUMBER OF SEQ ID NOS: 109

<210> SEQ ID NO 1
<211> LENGTH: 72
<212> TYPE: PRT
<213> ORGANISM: Triticum aestivum

<400> SEQUENCE: 1

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Met
        35                  40                  45

Glu Tyr Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 2
<211> LENGTH: 72
<212> TYPE: PRT
<213> ORGANISM: Artificial
<220> FEATURE:
<223> OTHER INFORMATION: Protease Inhibitor(B)

<400> SEQUENCE: 2

Thr Asp Thr Gly Asp His His Asn Gln Lys Thr Asp Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Met
        35                  40                  45

Glu Tyr Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 3
<211> LENGTH: 72
<212> TYPE: PRT
<213> ORGANISM: Artificial
<220> FEATURE:
<223> OTHER INFORMATION: Protease Inhibitor(B)

<400> SEQUENCE: 3

Thr Asp Thr Gly Asp His His Asn Gln Lys Thr Ala Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Met
        35                  40                  45

Glu Tyr Arg Ile Asp Arg Val Arg Leu Phe Val Asp Ser Leu Asp Lys
    50                  55                  60

Ile Ala Gln Val Pro Arg Val Gly
65                  70
```

```
<210> SEQ ID NO 4
<211> LENGTH: 72
<212> TYPE: PRT
<213> ORGANISM: Artificial
<220> FEATURE:
<223> OTHER INFORMATION: Protease Inhibitor(B)

<400> SEQUENCE: 4

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Ala Val Leu Pro Val Gly Thr Ile Val Thr Met
        35                  40                  45

Glu Tyr Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 5
<211> LENGTH: 72
<212> TYPE: PRT
<213> ORGANISM: Artificial
<220> FEATURE:
<223> OTHER INFORMATION: Protease Inhibitor(B)

<400> SEQUENCE: 5

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Leu Val Leu Pro Val Gly Thr Ile Val Thr Met
        35                  40                  45

Glu Tyr Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 6
<211> LENGTH: 72
<212> TYPE: PRT
<213> ORGANISM: Artificial
<220> FEATURE:
<223> OTHER INFORMATION: Protease Inhibitor(B)

<400> SEQUENCE: 6

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Ile Val Leu Pro Val Gly Thr Ile Val Thr Met
        35                  40                  45

Glu Tyr Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 7
<211> LENGTH: 72
```

<212> TYPE: PRT
<213> ORGANISM: Artificial
<220> FEATURE:
<223> OTHER INFORMATION: Protease Inhibitor(B)

<400> SEQUENCE: 7

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Ala
        35                  40                  45

Glu Tyr Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 8
<211> LENGTH: 72
<212> TYPE: PRT
<213> ORGANISM: Artificial
<220> FEATURE:
<223> OTHER INFORMATION: Protease Inhibitor(B)

<400> SEQUENCE: 8

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Gly
        35                  40                  45

Glu Tyr Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 9
<211> LENGTH: 72
<212> TYPE: PRT
<213> ORGANISM: Artificial
<220> FEATURE:
<223> OTHER INFORMATION: Protease Inhibitor(B)

<400> SEQUENCE: 9

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Met
        35                  40                  45

Glu Ala Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 10
<211> LENGTH: 72
<212> TYPE: PRT
<213> ORGANISM: Artificial
<220> FEATURE:
<223> OTHER INFORMATION: Protease Inhibitor(B)

<400> SEQUENCE: 10

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Met
        35                  40                  45

Glu Leu Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 11
<211> LENGTH: 72
<212> TYPE: PRT
<213> ORGANISM: Artificial
<220> FEATURE:
<223> OTHER INFORMATION: Protease Inhibitor(B)

<400> SEQUENCE: 11

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Met
        35                  40                  45

Glu Phe Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 12
<211> LENGTH: 72
<212> TYPE: PRT
<213> ORGANISM: Artificial
<220> FEATURE:
<223> OTHER INFORMATION: Protease Inhibitor(B)

<400> SEQUENCE: 12

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Met
        35                  40                  45

Glu Tyr Ala Ile Asp Arg Val Arg Leu Phe Val Asp Ser Leu Asp Lys
    50                  55                  60

Ile Ala Gln Val Pro Arg Val Gly
65                  70

<210> SEQ ID NO 13
<211> LENGTH: 72
<212> TYPE: PRT
<213> ORGANISM: Artificial
<220> FEATURE:
<223> OTHER INFORMATION: Protease Inhibitor(B)

<400> SEQUENCE: 13

Thr Asp Thr Gly Asp His His Asn Gln Lys Thr Glu Trp Pro Glu Leu

```
                1               5                      10                      15
Val Gly Lys Ser Val Glu Glu Ala Lys Lys Val Ile Leu Gln Asp Lys
                20                      25                      30

Ser Glu Ala Gln Ile Val Val Leu Pro Val Gly Thr Ile Val Thr Met
                35                      40                      45

Glu Tyr Lys Ile Asp Arg Val Arg Leu Phe Val Asp Ser Leu Asp Lys
                50                      55                      60

Ile Ala Gln Val Pro Arg Val Gly
65                      70

<210> SEQ ID NO 14
<211> LENGTH: 72
<212> TYPE: PRT
<213> ORGANISM: Artificial
<220> FEATURE:
<223> OTHER INFORMATION: Protease Inhibitor(B)

<400> SEQUENCE: 14

Thr Asp Thr Gly Asp His His Asn Gln Lys Thr Glu Trp Pro Glu Leu
1               5                       10                      15

Val Gly Lys Ser Val Glu Glu Ala Lys Lys Val Ile Leu Gln Asp Lys
                20                      25                      30

Ser Glu Ala Gln Ile Val Val Leu Pro Val Gly Thr Ile Val Thr Met
                35                      40                      45

Glu Tyr His Ile Asp Arg Val Arg Leu Phe Val Asp Ser Leu Asp Lys
                50                      55                      60

Ile Ala Gln Val Pro Arg Val Gly
65                      70

<210> SEQ ID NO 15
<211> LENGTH: 72
<212> TYPE: PRT
<213> ORGANISM: Artificial
<220> FEATURE:
<223> OTHER INFORMATION: Protease Inhibitor(B)

<400> SEQUENCE: 15

Thr Asp Thr Gly Asp His His Asn Gln Lys Thr Glu Trp Pro Glu Leu
1               5                       10                      15

Val Gly Lys Ser Val Glu Glu Ala Lys Lys Val Ile Leu Gln Asp Lys
                20                      25                      30

Ser Glu Ala Gln Ile Val Val Leu Pro Val Gly Thr Ile Val Thr Met
                35                      40                      45

Glu Tyr Arg Ala Asp Arg Val Arg Leu Phe Val Asp Ser Leu Asp Lys
                50                      55                      60

Ile Ala Gln Val Pro Arg Val Gly
65                      70

<210> SEQ ID NO 16
<211> LENGTH: 72
<212> TYPE: PRT
<213> ORGANISM: Artificial
<220> FEATURE:
<223> OTHER INFORMATION: Protease Inhibitor(B)

<400> SEQUENCE: 16

Thr Asp Thr Gly Asp His His Asn Gln Lys Thr Glu Trp Pro Glu Leu
1               5                       10                      15

Val Gly Lys Ser Val Glu Glu Ala Lys Lys Val Ile Leu Gln Asp Lys
                20                      25                      30
```

```
Ser Glu Ala Gln Ile Val Val Leu Pro Val Gly Thr Ile Val Thr Met
        35                  40                  45

Glu Tyr Arg Val Asp Arg Val Arg Leu Phe Val Ser Leu Asp Lys
 50                  55                  60

Ile Ala Gln Val Pro Arg Val Gly
 65                  70

<210> SEQ ID NO 17
<211> LENGTH: 72
<212> TYPE: PRT
<213> ORGANISM: Artificial
<220> FEATURE:
<223> OTHER INFORMATION: Protease Inhibitor(B)

<400> SEQUENCE: 17

Thr Asp Thr Gly Asp His His Asn Gln Lys Thr Glu Trp Pro Glu Leu
 1               5                  10                  15

Val Gly Lys Ser Val Glu Glu Ala Lys Lys Val Ile Leu Gln Asp Lys
                20                  25                  30

Ser Glu Ala Gln Ile Val Val Leu Pro Val Gly Thr Ile Val Thr Met
        35                  40                  45

Glu Tyr Arg Ile Glu Arg Val Arg Leu Phe Val Ser Leu Asp Lys
 50                  55                  60

Ile Ala Gln Val Pro Arg Val Gly
 65                  70

<210> SEQ ID NO 18
<211> LENGTH: 72
<212> TYPE: PRT
<213> ORGANISM: Artificial
<220> FEATURE:
<223> OTHER INFORMATION: Protease Inhibitor(B)

<400> SEQUENCE: 18

Thr Asp Thr Gly Asp His His Asn Gln Lys Thr Glu Trp Pro Glu Leu
 1               5                  10                  15

Val Gly Lys Ser Val Glu Glu Ala Lys Lys Val Ile Leu Gln Asp Lys
                20                  25                  30

Ser Glu Ala Gln Ile Val Val Leu Pro Val Gly Thr Ile Val Thr Met
        35                  40                  45

Glu Tyr Arg Ile Ala Arg Val Arg Leu Phe Val Ser Leu Asp Lys
 50                  55                  60

Ile Ala Gln Val Pro Arg Val Gly
 65                  70

<210> SEQ ID NO 19
<211> LENGTH: 72
<212> TYPE: PRT
<213> ORGANISM: Artificial
<220> FEATURE:
<223> OTHER INFORMATION: Protease Inhibitor(B)

<400> SEQUENCE: 19

Thr Asp Thr Gly Asp His His Asn Gln Lys Thr Glu Trp Pro Glu Leu
 1               5                  10                  15

Val Gly Lys Ser Val Glu Glu Ala Lys Lys Val Ile Leu Gln Asp Lys
                20                  25                  30

Ser Glu Ala Gln Ile Val Val Leu Pro Val Gly Thr Ile Val Thr Met
        35                  40                  45
```

```
Glu Tyr Arg Ile Asp Arg Val Arg Leu Phe Val Asp Ser Leu Asp Lys
 50                  55                  60

Ile Ala Gln Val Pro Ala Val Gly
 65                  70

<210> SEQ ID NO 20
<211> LENGTH: 72
<212> TYPE: PRT
<213> ORGANISM: Artificial
<220> FEATURE:
<223> OTHER INFORMATION: Protease Inhibitor(B)

<400> SEQUENCE: 20

Thr Asp Thr Gly Asp His His Asn Gln Lys Thr Glu Trp Pro Glu Leu
 1               5                  10                  15

Val Gly Lys Ser Val Glu Glu Ala Lys Lys Val Ile Leu Gln Asp Lys
             20                  25                  30

Ser Glu Ala Gln Ile Val Val Leu Pro Val Gly Thr Ile Val Thr Met
         35                  40                  45

Glu Tyr Arg Ile Asp Arg Val Arg Leu Phe Val Asp Ser Leu Asp Lys
 50                  55                  60

Ile Ala Gln Val Pro Gly Val Gly
 65                  70

<210> SEQ ID NO 21
<211> LENGTH: 72
<212> TYPE: PRT
<213> ORGANISM: Artificial
<220> FEATURE:
<223> OTHER INFORMATION: Protease Inhibitor(B)

<400> SEQUENCE: 21

Thr Asp Thr Gly Asp His His Asn Gln Lys Thr Glu Trp Pro Glu Leu
 1               5                  10                  15

Val Gly Lys Ser Val Glu Glu Ala Lys Lys Val Ile Leu Gln Asp Lys
             20                  25                  30

Ser Glu Ala Gln Ile Val Val Leu Pro Val Gly Thr Ile Val Thr Met
         35                  40                  45

Glu Tyr Arg Ile Asp Arg Val Arg Leu Phe Val Asp Ser Leu Asp Lys
 50                  55                  60

Ile Ala Gln Val Pro Lys Val Gly
 65                  70

<210> SEQ ID NO 22
<211> LENGTH: 72
<212> TYPE: PRT
<213> ORGANISM: Artificial
<220> FEATURE:
<223> OTHER INFORMATION: Protease Inhibitor(B)

<400> SEQUENCE: 22

Thr Asp Thr Gly Asp His His Asn Gln Lys Thr Glu Trp Pro Glu Leu
 1               5                  10                  15

Val Gly Lys Ser Val Glu Glu Ala Lys Lys Val Ile Leu Gln Asp Lys
             20                  25                  30

Ser Glu Ala Gln Ile Ala Val Leu Pro Val Gly Thr Ile Val Thr Met
         35                  40                  45

Glu Tyr Ala Ala Asp Arg Val Arg Leu Phe Val Asp Ser Leu Asp Lys
 50                  55                  60

Ile Ala Gln Val Pro Arg Val Gly
```

65          70

<210> SEQ ID NO 23
<211> LENGTH: 72
<212> TYPE: PRT
<213> ORGANISM: Artificial
<220> FEATURE:
<223> OTHER INFORMATION: Protease Inhibitor(B)

<400> SEQUENCE: 23

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Ala Val Leu Pro Val Gly Thr Ile Val Thr Met
        35                  40                  45

Glu Tyr Arg Ala Ala Arg Val Arg Leu Phe Val Asp Ser Leu Asp Lys
    50                  55                  60

Ile Ala Gln Val Pro Arg Val Gly
65                  70

<210> SEQ ID NO 24
<211> LENGTH: 72
<212> TYPE: PRT
<213> ORGANISM: Artificial
<220> FEATURE:
<223> OTHER INFORMATION: Protease Inhibitor(B)

<400> SEQUENCE: 24

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Gly
        35                  40                  45

Glu Tyr Arg Ile Asp Arg Val Arg Leu Phe Val Asp Ser Leu Asp Lys
    50                  55                  60

Ile Ala Gln Val Pro Ala Val Gly
65                  70

<210> SEQ ID NO 25
<211> LENGTH: 72
<212> TYPE: PRT
<213> ORGANISM: Artificial
<220> FEATURE:
<223> OTHER INFORMATION: Protease Inhibitor(B)

<400> SEQUENCE: 25

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Ala Val Leu Pro Val Gly Thr Ile Val Thr Met
        35                  40                  45

Glu Tyr Arg Ile Asp Arg Val Arg Leu Phe Val Asp Ser Leu Asp Lys
    50                  55                  60

Ile Ala Gln Val Pro Ala Val Gly
65                  70

<210> SEQ ID NO 26

```
<211> LENGTH: 72
<212> TYPE: PRT
<213> ORGANISM: Artificial
<220> FEATURE:
<223> OTHER INFORMATION: Protease Inhibitor(B)

<400> SEQUENCE: 26

Thr Asp Thr Gly Asp His His Asn Gln Lys Thr Asp Trp Pro Glu Leu
1               5                   10                  15

Val Gly Lys Ser Val Glu Glu Ala Pro Lys Val Ile Leu Gln Asp Lys
            20                  25                  30

Ser Glu Ala Pro Ile Ala Val Leu Pro Val Gly Thr Leu Val Thr Ala
        35                  40                  45

Glu Ala Ala Ala Arg Val Arg Leu Phe Val Asp Ser Leu Asp Lys
    50                  55                  60

Ile Ala Gln Val Pro Ala Val Gly
65                  70

<210> SEQ ID NO 27
<211> LENGTH: 72
<212> TYPE: PRT
<213> ORGANISM: Artificial
<220> FEATURE:
<223> OTHER INFORMATION: Protease Inhibitor(B)

<400> SEQUENCE: 27

Thr Asp Thr Gly Asp His His Asn Gln Lys Thr Lys Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Met
        35                  40                  45

Glu Tyr Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 28
<211> LENGTH: 72
<212> TYPE: PRT
<213> ORGANISM: Artificial
<220> FEATURE:
<223> OTHER INFORMATION: Protease Inhibitor(B)

<400> SEQUENCE: 28

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Met
        35                  40                  45

Glu Gly Arg Ile Asp Arg Val Arg Leu Phe Val Asp Ser Leu Asp Lys
    50                  55                  60

Ile Ala Gln Val Pro Arg Val Gly
65                  70

<210> SEQ ID NO 29
<211> LENGTH: 72
<212> TYPE: PRT
<213> ORGANISM: Artificial
<220> FEATURE:
```

<223> OTHER INFORMATION: Protease Inhibitor(B)

<400> SEQUENCE: 29

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Val Val Leu Pro Val Gly Thr Ile Val Thr Met
        35                  40                  45

Glu Tyr Arg Ile Asp Arg Val Arg Leu Phe Val Asp Ser Leu Asp Lys
    50                  55                  60

Ile Ala Gln Val Pro Asn Val Gly
65                  70

<210> SEQ ID NO 30
<211> LENGTH: 84
<212> TYPE: PRT
<213> ORGANISM: Artificial
<220> FEATURE:
<223> OTHER INFORMATION: Protease Inhibitor(C)

<400> SEQUENCE: 30

Met Ser Ser Val Glu Lys Lys Pro Glu Gly Val Asn Thr Gly Ala Gly
1               5                   10                  15

Asp Arg His Asn Leu Lys Thr Ala Trp Pro Glu Leu Val Gly Lys Ser
            20                  25                  30

Val Glu Glu Ala Lys Lys Val Ile Leu Gln Asp Lys Ser Glu Ala Gln
        35                  40                  45

Ile Ile Val Leu Pro Val Gly Thr Ile Val Thr Met Glu Tyr Arg Ile
    50                  55                  60

Asp Arg Val Arg Leu Phe Val Asp Lys Leu Asp Asn Ile Ala Gln Val
65                  70                  75                  80

Pro Arg Val Gly

<210> SEQ ID NO 31
<211> LENGTH: 84
<212> TYPE: PRT
<213> ORGANISM: Artificial
<220> FEATURE:
<223> OTHER INFORMATION: Protease Inhibitor(C)

<400> SEQUENCE: 31

Met Ser Ser Val Glu Lys Lys Pro Glu Gly Val Asn Thr Gly Ala Gly
1               5                   10                  15

Asp Arg His Asn Leu Lys Thr Glu Trp Pro Glu Leu Val Gly Lys Ser
            20                  25                  30

Val Glu Glu Ala Lys Lys Val Ile Leu Gln Asp Lys Ser Glu Ala Gln
        35                  40                  45

Ile Ala Val Leu Pro Val Gly Thr Ile Val Thr Met Glu Tyr Arg Ile
    50                  55                  60

Asp Arg Val Arg Leu Phe Val Asp Lys Leu Asp Asn Ile Ala Gln Val
65                  70                  75                  80

Pro Arg Val Gly

<210> SEQ ID NO 32
<211> LENGTH: 84
<212> TYPE: PRT
<213> ORGANISM: Artificial
<220> FEATURE:

<223> OTHER INFORMATION: Protease Inhibitor(C)

<400> SEQUENCE: 32

Met Ser Ser Val Glu Lys Lys Pro Glu Gly Val Asn Thr Gly Ala Gly
1               5                   10                  15

Asp Arg His Asn Leu Lys Thr Glu Trp Pro Glu Leu Val Gly Lys Ser
            20                  25                  30

Val Glu Glu Ala Lys Lys Val Ile Leu Gln Asp Lys Ser Glu Ala Gln
        35                  40                  45

Ile Ile Val Leu Pro Val Gly Thr Ile Val Thr Met Glu Ala Arg Ile
    50                  55                  60

Asp Arg Val Arg Leu Phe Val Asp Lys Leu Asp Asn Ile Ala Gln Val
65                  70                  75                  80

Pro Arg Val Gly

<210> SEQ ID NO 33
<211> LENGTH: 84
<212> TYPE: PRT
<213> ORGANISM: Artificial
<220> FEATURE:
<223> OTHER INFORMATION: Protease Inhibitor(C)

<400> SEQUENCE: 33

Met Ser Ser Val Glu Lys Lys Pro Glu Gly Val Asn Thr Gly Ala Gly
1               5                   10                  15

Asp Arg His Asn Leu Lys Thr Glu Trp Pro Glu Leu Val Gly Lys Ser
            20                  25                  30

Val Glu Glu Ala Lys Lys Val Ile Leu Gln Asp Lys Ser Glu Ala Gln
        35                  40                  45

Ile Ile Val Leu Pro Val Gly Thr Ile Val Thr Met Glu Tyr Ala Ile
    50                  55                  60

Asp Arg Val Arg Leu Phe Val Asp Lys Leu Asp Asn Ile Ala Gln Val
65                  70                  75                  80

Pro Arg Val Gly

<210> SEQ ID NO 34
<211> LENGTH: 84
<212> TYPE: PRT
<213> ORGANISM: Artificial
<220> FEATURE:
<223> OTHER INFORMATION: Protease Inhibitor(C)

<400> SEQUENCE: 34

Met Ser Ser Val Glu Lys Lys Pro Glu Gly Val Asn Thr Gly Ala Gly
1               5                   10                  15

Asp Arg His Asn Leu Lys Thr Glu Trp Pro Glu Leu Val Gly Lys Ser
            20                  25                  30

Val Glu Glu Ala Lys Lys Val Ile Leu Gln Asp Lys Ser Glu Ala Gln
        35                  40                  45

Ile Ile Val Leu Pro Val Gly Thr Ile Val Thr Met Glu Tyr Arg Ala
    50                  55                  60

Asp Arg Val Arg Leu Phe Val Asp Lys Leu Asp Asn Ile Ala Gln Val
65                  70                  75                  80

Pro Arg Val Gly

<210> SEQ ID NO 35
<211> LENGTH: 84
<212> TYPE: PRT

<213> ORGANISM: Artificial
<220> FEATURE:
<223> OTHER INFORMATION: Protease Inhibitor(C)

<400> SEQUENCE: 35

```
Met Ser Ser Val Glu Lys Lys Pro Glu Gly Val Asn Thr Gly Ala Gly
1               5                   10                  15

Asp Arg His Asn Leu Lys Thr Glu Trp Pro Glu Leu Val Gly Lys Ser
            20                  25                  30

Val Glu Glu Ala Lys Lys Val Ile Leu Gln Asp Lys Ser Glu Ala Gln
        35                  40                  45

Ile Ile Val Leu Pro Val Gly Thr Ile Val Thr Met Glu Tyr Arg Ile
50                  55                  60

Ala Arg Val Arg Leu Phe Val Asp Lys Leu Asp Asn Ile Ala Gln Val
65                  70                  75                  80

Pro Arg Val Gly
```

<210> SEQ ID NO 36
<211> LENGTH: 84
<212> TYPE: PRT
<213> ORGANISM: Artificial
<220> FEATURE:
<223> OTHER INFORMATION: Protease Inhibitor(C)

<400> SEQUENCE: 36

```
Met Ser Ser Val Glu Lys Lys Pro Glu Gly Val Asn Thr Gly Ala Gly
1               5                   10                  15

Asp Arg His Asn Leu Lys Thr Glu Trp Pro Glu Leu Val Gly Lys Ser
            20                  25                  30

Val Glu Glu Ala Lys Lys Val Ile Leu Gln Asp Lys Ser Glu Ala Gln
        35                  40                  45

Ile Ile Val Leu Pro Val Gly Thr Ile Val Thr Met Glu Tyr Arg Ile
50                  55                  60

Asp Arg Val Arg Leu Phe Val Asp Lys Leu Asp Asn Ile Ala Gln Val
65                  70                  75                  80

Pro Ala Val Gly
```

<210> SEQ ID NO 37
<211> LENGTH: 72
<212> TYPE: PRT
<213> ORGANISM: Artificial
<220> FEATURE:
<223> OTHER INFORMATION: Protease Inhibitor(B)

<400> SEQUENCE: 37

```
Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
            20                  25                  30

Ser Glu Ala Gln Ile Ala Val Leu Pro Val Gly Thr Ile Val Thr Met
        35                  40                  45

Glu Tyr Ala Ile Asp Arg Val Arg Leu Phe Val Asp Ser Leu Asp Lys
50                  55                  60

Ile Ala Gln Val Pro Arg Val Gly
65                  70
```

<210> SEQ ID NO 38
<211> LENGTH: 72
<212> TYPE: PRT

```
<213> ORGANISM: Artificial
<220> FEATURE:
<223> OTHER INFORMATION: Protease Inhibitor(B)

<400> SEQUENCE: 38

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
                20                  25                  30

Ser Glu Ala Gln Ile Ala Val Leu Pro Val Gly Thr Ile Val Thr Met
            35                  40                  45

Glu Tyr Arg Ala Asp Arg Val Arg Leu Phe Val Asp Ser Leu Asp Lys
    50                  55                  60

Ile Ala Gln Val Pro Arg Val Gly
65                  70

<210> SEQ ID NO 39
<211> LENGTH: 72
<212> TYPE: PRT
<213> ORGANISM: Artificial
<220> FEATURE:
<223> OTHER INFORMATION: Protease Inhibitor(B)

<400> SEQUENCE: 39

Thr Asp Thr Gly Asp His His Asn Gln Lys Thr Glu Trp Pro Glu Leu
1               5                   10                  15

Val Gly Lys Ser Val Glu Glu Ala Lys Lys Val Ile Leu Gln Asp Lys
                20                  25                  30

Ser Glu Ala Gln Ile Ala Val Leu Pro Val Gly Thr Ile Val Thr Ala
            35                  40                  45

Glu Tyr Arg Ile Ala Arg Val Arg Leu Phe Val Asp Ser Leu Asp Lys
    50                  55                  60

Ile Ala Gln Val Pro Arg Val Gly
65                  70

<210> SEQ ID NO 40
<211> LENGTH: 69
<212> TYPE: PRT
<213> ORGANISM: Artificial
<220> FEATURE:
<223> OTHER INFORMATION: Protease Inhibitor

<400> SEQUENCE: 40

Thr Glu Cys Gly Gly Gly Gly Ala Lys Thr Ser Trp Pro Glu Val
1               5                   10                  15

Val Gly Leu Ser Val Glu Glu Ala Lys Lys Val Ile Leu Lys Asp Lys
                20                  25                  30

Pro Asp Ala Asp Ile Val Val Leu Pro Val Gly Ser Val Thr Ala
            35                  40                  45

Asp Tyr Arg Pro Asn Arg Val Arg Ile Phe Val Asp Ile Val Ala Gln
    50                  55                  60

Thr Pro His Val Gly
65

<210> SEQ ID NO 41
<211> LENGTH: 84
<212> TYPE: PRT
<213> ORGANISM: Artificial
<220> FEATURE:
<223> OTHER INFORMATION: Synthetic Construct
```

<400> SEQUENCE: 41

Met Ser Ser Val Glu Lys Lys Pro Glu Gly Val Asn Thr Gly Ala Gly
1               5                   10                  15

Asp Arg His Asn Leu Lys Thr Glu Trp Pro Glu Leu Val Gly Lys Ser
            20                  25                  30

Val Glu Glu Ala Lys Lys Val Ile Leu Gln Asp Lys Ser Glu Ala Gln
        35                  40                  45

Ile Ile Val Leu Pro Val Gly Thr Ile Val Thr Met Glu Tyr Arg Ile
    50                  55                  60

Asp Arg Val Arg Leu Phe Val Asp Lys Leu Asp Asn Ile Ala Gln Val
65                  70                  75                  80

Pro Arg Val Gly

<210> SEQ ID NO 42
<211> LENGTH: 30
<212> TYPE: DNA
<213> ORGANISM: Artificial
<220> FEATURE:
<223> OTHER INFORMATION: Primer

<400> SEQUENCE: 42
cagaaaactg attggcctga actggttggt                               30

<210> SEQ ID NO 43
<211> LENGTH: 30
<212> TYPE: DNA
<213> ORGANISM: Artificial
<220> FEATURE:
<223> OTHER INFORMATION: Primer

<400> SEQUENCE: 43
tcaggccaat cagttttctg gttgtgatga                               30

<210> SEQ ID NO 44
<211> LENGTH: 30
<212> TYPE: DNA
<213> ORGANISM: Artificial
<220> FEATURE:
<223> OTHER INFORMATION: Primer

<400> SEQUENCE: 44
cagaaaactg catggcctga actggttggt                               30

<210> SEQ ID NO 45
<211> LENGTH: 30
<212> TYPE: DNA
<213> ORGANISM: Artificial
<220> FEATURE:
<223> OTHER INFORMATION: Primer

<400> SEQUENCE: 45
tcaggccatg cagttttctg gttgtgatga                               30

<210> SEQ ID NO 46
<211> LENGTH: 30
<212> TYPE: DNA
<213> ORGANISM: Artificial
<220> FEATURE:
<223> OTHER INFORMATION: Primer

<400> SEQUENCE: 46
gcgcagattg cggtactgcc agttggcacc                               30

<210> SEQ ID NO 47
<211> LENGTH: 30
<212> TYPE: DNA
<213> ORGANISM: Artificial
<220> FEATURE:
<223> OTHER INFORMATION: Primer

<400> SEQUENCE: 47
ggcagtaccg caatctgcgc ttcagatttg                                    30

<210> SEQ ID NO 48
<211> LENGTH: 30
<212> TYPE: DNA
<213> ORGANISM: Artificial
<220> FEATURE:
<223> OTHER INFORMATION: Primer

<400> SEQUENCE: 48
gcgcagattt tagtactgcc agttggcacc                                    30

<210> SEQ ID NO 49
<211> LENGTH: 30
<212> TYPE: DNA
<213> ORGANISM: Artificial
<220> FEATURE:
<223> OTHER INFORMATION: Primer

<400> SEQUENCE: 49
ggcagtacta aaatctgcgc ttcagatttg                                    30

<210> SEQ ID NO 50
<211> LENGTH: 30
<212> TYPE: DNA
<213> ORGANISM: Artificial
<220> FEATURE:
<223> OTHER INFORMATION: Primer

<400> SEQUENCE: 50
gcgcagatta tagtactgcc agttggcacc                                    30

<210> SEQ ID NO 51
<211> LENGTH: 30
<212> TYPE: DNA
<213> ORGANISM: Artificial
<220> FEATURE:
<223> OTHER INFORMATION: Primer

<400> SEQUENCE: 51
ggcagtacta taatctgcgc ttcagatttg                                    30

<210> SEQ ID NO 52
<211> LENGTH: 30
<212> TYPE: DNA
<213> ORGANISM: Artificial
<220> FEATURE:
<223> OTHER INFORMATION: Primer

<400> SEQUENCE: 52
atcgtgactg cagagtaccg tatcgaccgt                                    30

<210> SEQ ID NO 53
<211> LENGTH: 30
<212> TYPE: DNA
<213> ORGANISM: Artificial
<220> FEATURE:
<223> OTHER INFORMATION: Primer

<400> SEQUENCE: 53
cggtactctg cagtcacgat ggtgccaact                              30

<210> SEQ ID NO 54
<211> LENGTH: 30
<212> TYPE: DNA
<213> ORGANISM: Artificial
<220> FEATURE:
<223> OTHER INFORMATION: Primer

<400> SEQUENCE: 54
atcgtgactg gggagtaccg tatcgaccgt                              30

<210> SEQ ID NO 55
<211> LENGTH: 30
<212> TYPE: DNA
<213> ORGANISM: Artificial
<220> FEATURE:
<223> OTHER INFORMATION: Primer

<400> SEQUENCE: 55
cggtactccc cagtcacgat ggtgccaact                              30

<210> SEQ ID NO 56
<211> LENGTH: 30
<212> TYPE: DNA
<213> ORGANISM: Artificial
<220> FEATURE:
<223> OTHER INFORMATION: Primer

<400> SEQUENCE: 56
actatggagg cccgtatcga ccgtgttcgt                              30

<210> SEQ ID NO 57
<211> LENGTH: 30
<212> TYPE: DNA
<213> ORGANISM: Artificial
<220> FEATURE:
<223> OTHER INFORMATION: Primer

<400> SEQUENCE: 57
tcgatacggg cctccatagt cacgatggtg                              30

<210> SEQ ID NO 58
<211> LENGTH: 30
<212> TYPE: DNA
<213> ORGANISM: Artificial
<220> FEATURE:
<223> OTHER INFORMATION: Primer

<400> SEQUENCE: 58
actatggagt tacgtatcga ccgtgttcgt                              30

<210> SEQ ID NO 59
<211> LENGTH: 30
<212> TYPE: DNA
<213> ORGANISM: Artificial
<220> FEATURE:
<223> OTHER INFORMATION: Primer

<400> SEQUENCE: 59
tcgatacgta actccatagt cacgatggtg                              30

<210> SEQ ID NO 60

```
<211> LENGTH: 30
<212> TYPE: DNA
<213> ORGANISM: Artificial
<220> FEATURE:
<223> OTHER INFORMATION: Primer

<400> SEQUENCE: 60
actatggagt tccgtatcga ccgtgttcgt                                          30

<210> SEQ ID NO 61
<211> LENGTH: 30
<212> TYPE: DNA
<213> ORGANISM: Artificial
<220> FEATURE:
<223> OTHER INFORMATION: Primer

<400> SEQUENCE: 61
tcgatacgga actccatagt cacgatggtg                                          30

<210> SEQ ID NO 62
<211> LENGTH: 35
<212> TYPE: DNA
<213> ORGANISM: Artificial
<220> FEATURE:
<223> OTHER INFORMATION: Primer

<400> SEQUENCE: 62
tatggagtac gcaatagacc gtgttcgtct gttcg                                    35

<210> SEQ ID NO 63
<211> LENGTH: 35
<212> TYPE: DNA
<213> ORGANISM: Artificial
<220> FEATURE:
<223> OTHER INFORMATION: Primer

<400> SEQUENCE: 63
gaacacggtc tattgcgtac tccatagtca cgatg                                    35

<210> SEQ ID NO 64
<211> LENGTH: 35
<212> TYPE: DNA
<213> ORGANISM: Artificial
<220> FEATURE:
<223> OTHER INFORMATION: Primer

<400> SEQUENCE: 64
tatggagtac aaaatagacc gtgttcgtct gttcg                                    35

<210> SEQ ID NO 65
<211> LENGTH: 35
<212> TYPE: DNA
<213> ORGANISM: Artificial
<220> FEATURE:
<223> OTHER INFORMATION: Primer

<400> SEQUENCE: 65
gaacacggtc tattttgtac tccatagtca cgatg                                    35

<210> SEQ ID NO 66
<211> LENGTH: 35
<212> TYPE: DNA
<213> ORGANISM: Artificial
<220> FEATURE:
<223> OTHER INFORMATION: Primer

<400> SEQUENCE: 66
```

```
tatggagtac cacatagacc gtgttcgtct gttcg                          35

<210> SEQ ID NO 67
<211> LENGTH: 35
<212> TYPE: DNA
<213> ORGANISM: Artificial
<220> FEATURE:
<223> OTHER INFORMATION: Primer

<400> SEQUENCE: 67
gaacacggtc tatgtggtac tccatagtca cgatg                          35

<210> SEQ ID NO 68
<211> LENGTH: 35
<212> TYPE: DNA
<213> ORGANISM: Artificial
<220> FEATURE:
<223> OTHER INFORMATION: Primer

<400> SEQUENCE: 68
ggagtaccgt gccgaccgtg ttcgtctgtt cgttg                          35

<210> SEQ ID NO 69
<211> LENGTH: 32
<212> TYPE: DNA
<213> ORGANISM: Artificial
<220> FEATURE:
<223> OTHER INFORMATION: Primer

<400> SEQUENCE: 69
gaacacgctg ggcacggtac tccatagtca cg                             32

<210> SEQ ID NO 70
<211> LENGTH: 35
<212> TYPE: DNA
<213> ORGANISM: Artificial
<220> FEATURE:
<223> OTHER INFORMATION: Primer

<400> SEQUENCE: 70
ggagtaccgt gtagaccgtg ttcgtctgtt cgttg                          35

<210> SEQ ID NO 71
<211> LENGTH: 32
<212> TYPE: DNA
<213> ORGANISM: Artificial
<220> FEATURE:
<223> OTHER INFORMATION: Primer

<400> SEQUENCE: 71
gaacacgctg tacacggtac tccatagtca cg                             32

<210> SEQ ID NO 72
<211> LENGTH: 35
<212> TYPE: DNA
<213> ORGANISM: Artificial
<220> FEATURE:
<223> OTHER INFORMATION: Primer

<400> SEQUENCE: 72
ggagtaccgt atagaacgtg ttcgtctgtt cgttg                          35

<210> SEQ ID NO 73
<211> LENGTH: 35
<212> TYPE: DNA
```

<213> ORGANISM: Artificial
<220> FEATURE:
<223> OTHER INFORMATION: Primer

<400> SEQUENCE: 73
gacgaacacg ttctatacgg tactccatag tcacg                        35

<210> SEQ ID NO 74
<211> LENGTH: 35
<212> TYPE: DNA
<213> ORGANISM: Artificial
<220> FEATURE:
<223> OTHER INFORMATION: Primer

<400> SEQUENCE: 74
ggagtaccgt atagcccgtg ttcgtctgtt cgttg                        35

<210> SEQ ID NO 75
<211> LENGTH: 35
<212> TYPE: DNA
<213> ORGANISM: Artificial
<220> FEATURE:
<223> OTHER INFORMATION: Primer

<400> SEQUENCE: 75
gacgaacacg ggctatacgg tactccatag tcacg                        35

<210> SEQ ID NO 76
<211> LENGTH: 30
<212> TYPE: DNA
<213> ORGANISM: Artificial
<220> FEATURE:
<223> OTHER INFORMATION: Primer

<400> SEQUENCE: 76
caggtgccgg ccgtgggtta aggatccgaa                              30

<210> SEQ ID NO 77
<211> LENGTH: 30
<212> TYPE: DNA
<213> ORGANISM: Artificial
<220> FEATURE:
<223> OTHER INFORMATION: Primer

<400> SEQUENCE: 77
taacccacgg ccggcacctg agcaattttg                              30

<210> SEQ ID NO 78
<211> LENGTH: 30
<212> TYPE: DNA
<213> ORGANISM: Artificial
<220> FEATURE:
<223> OTHER INFORMATION: Primer

<400> SEQUENCE: 78
caggtgccgg gcgtgggtta aggatccgaa                              30

<210> SEQ ID NO 79
<211> LENGTH: 30
<212> TYPE: DNA
<213> ORGANISM: Artificial
<220> FEATURE:
<223> OTHER INFORMATION: Primer

<400> SEQUENCE: 79
taacccacgc ccggcacctg agcaattttg                              30

<210> SEQ ID NO 80
<211> LENGTH: 30
<212> TYPE: DNA
<213> ORGANISM: Artificial
<220> FEATURE:
<223> OTHER INFORMATION: Primer

<400> SEQUENCE: 80
caggtgccga aagtgggtta aggatccgaa                                    30

<210> SEQ ID NO 81
<211> LENGTH: 30
<212> TYPE: DNA
<213> ORGANISM: Artificial
<220> FEATURE:
<223> OTHER INFORMATION: Primer

<400> SEQUENCE: 81
taacccactt tcggcacctg agcaattttg                                    30

<210> SEQ ID NO 82
<211> LENGTH: 35
<212> TYPE: DNA
<213> ORGANISM: Artificial
<220> FEATURE:
<223> OTHER INFORMATION: Primer

<400> SEQUENCE: 82
tatggagtac gccgcggacc gtgttcgtct gttcg                              35

<210> SEQ ID NO 83
<211> LENGTH: 35
<212> TYPE: DNA
<213> ORGANISM: Artificial
<220> FEATURE:
<223> OTHER INFORMATION: Primer

<400> SEQUENCE: 83
gaacacggtc cgcggcgtac tccatagtca cgatg                              35

<210> SEQ ID NO 84
<211> LENGTH: 35
<212> TYPE: DNA
<213> ORGANISM: Artificial
<220> FEATURE:
<223> OTHER INFORMATION: Primer

<400> SEQUENCE: 84
ggagtaccgt gccgcccgtg ttcgtctgtt cgttg                              35

<210> SEQ ID NO 85
<211> LENGTH: 35
<212> TYPE: DNA
<213> ORGANISM: Artificial
<220> FEATURE:
<223> OTHER INFORMATION: Primer

<400> SEQUENCE: 85
gacgaacacg ggcggcacgg tactccatag tcacg                              35

<210> SEQ ID NO 86
<211> LENGTH: 30
<212> TYPE: DNA
<213> ORGANISM: Artificial
<220> FEATURE:

<223> OTHER INFORMATION: Primer

<400> SEQUENCE: 86
cagaaaacta aatggcctga actggttggt                                30

<210> SEQ ID NO 87
<211> LENGTH: 30
<212> TYPE: DNA
<213> ORGANISM: Artificial
<220> FEATURE:
<223> OTHER INFORMATION: Primer

<400> SEQUENCE: 87
tcaggccatt tagttttctg gttgtgatga                                30

<210> SEQ ID NO 88
<211> LENGTH: 30
<212> TYPE: DNA
<213> ORGANISM: Artificial
<220> FEATURE:
<223> OTHER INFORMATION: Primer

<400> SEQUENCE: 88
actatggagg ggcgtatcga ccgtgttcgt                                30

<210> SEQ ID NO 89
<211> LENGTH: 30
<212> TYPE: DNA
<213> ORGANISM: Artificial
<220> FEATURE:
<223> OTHER INFORMATION: Primer

<400> SEQUENCE: 89
tcgatacgcc cctccatagt cacgatggtg                                30

<210> SEQ ID NO 90
<211> LENGTH: 30
<212> TYPE: DNA
<213> ORGANISM: Artificial
<220> FEATURE:
<223> OTHER INFORMATION: Primer

<400> SEQUENCE: 90
caggtgccga atgtgggtta aggatccgaa                                30

<210> SEQ ID NO 91
<211> LENGTH: 30
<212> TYPE: DNA
<213> ORGANISM: Artificial
<220> FEATURE:
<223> OTHER INFORMATION: Primer

<400> SEQUENCE: 91
taacccacat tcggcacctg agcaattttg                                30

<210> SEQ ID NO 92
<211> LENGTH: 30
<212> TYPE: DNA
<213> ORGANISM: Artificial
<220> FEATURE:
<223> OTHER INFORMATION: Primer

<400> SEQUENCE: 92
ctgaagacag cgtggccaga gttggtgggg                                30

<210> SEQ ID NO 93
<211> LENGTH: 30
<212> TYPE: DNA
<213> ORGANISM: Artificial
<220> FEATURE:
<223> OTHER INFORMATION: Primer

<400> SEQUENCE: 93
tctggccacg ctgtcttcag gttgtgacgg                           30

<210> SEQ ID NO 94
<211> LENGTH: 30
<212> TYPE: DNA
<213> ORGANISM: Artificial
<220> FEATURE:
<223> OTHER INFORMATION: Primer

<400> SEQUENCE: 94
ggcgcaaatc gcagttctgc cggtggggac                           30

<210> SEQ ID NO 95
<211> LENGTH: 31
<212> TYPE: DNA
<213> ORGANISM: Artificial
<220> FEATURE:
<223> OTHER INFORMATION: Primer

<400> SEQUENCE: 95
ggcagaactg cgatttgcgc ctctgacttg t                         31

<210> SEQ ID NO 96
<211> LENGTH: 30
<212> TYPE: DNA
<213> ORGANISM: Artificial
<220> FEATURE:
<223> OTHER INFORMATION: Primer

<400> SEQUENCE: 96
gaccatggaa gctcggatcg accgcgtccg                           30

<210> SEQ ID NO 97
<211> LENGTH: 29
<212> TYPE: DNA
<213> ORGANISM: Artificial
<220> FEATURE:
<223> OTHER INFORMATION: Primer

<400> SEQUENCE: 97
gtcgatccga gcttccatgg tcacaattg                            29

<210> SEQ ID NO 98
<211> LENGTH: 29
<212> TYPE: DNA
<213> ORGANISM: Artificial
<220> FEATURE:
<223> OTHER INFORMATION: Primer

<400> SEQUENCE: 98
ccatggaata tgcgatcgac cgcgtccgc                            29

<210> SEQ ID NO 99
<211> LENGTH: 30
<212> TYPE: DNA
<213> ORGANISM: Artificial
<220> FEATURE:
<223> OTHER INFORMATION: Primer

<400> SEQUENCE: 99
ggtcgatcgc atattccatg gtcacaattg    30

<210> SEQ ID NO 100
<211> LENGTH: 30
<212> TYPE: DNA
<213> ORGANISM: Artificial
<220> FEATURE:
<223> OTHER INFORMATION: Primer

<400> SEQUENCE: 100
gaatatcggg ccgaccgcgt ccgcctcttt    30

<210> SEQ ID NO 101
<211> LENGTH: 30
<212> TYPE: DNA
<213> ORGANISM: Artificial
<220> FEATURE:
<223> OTHER INFORMATION: Primer

<400> SEQUENCE: 101
acgcggtcgg cccgatattc catggtcaca    30

<210> SEQ ID NO 102
<211> LENGTH: 30
<212> TYPE: DNA
<213> ORGANISM: Artificial
<220> FEATURE:
<223> OTHER INFORMATION: Primer

<400> SEQUENCE: 102
tatcggatcg cccgcgtccg cctctttgtc    30

<210> SEQ ID NO 103
<211> LENGTH: 31
<212> TYPE: DNA
<213> ORGANISM: Artificial
<220> FEATURE:
<223> OTHER INFORMATION: Primer

<400> SEQUENCE: 103
cggacgcggg cgatccgata ttccatggtc a    31

<210> SEQ ID NO 104
<211> LENGTH: 20
<212> TYPE: DNA
<213> ORGANISM: Artificial
<220> FEATURE:
<223> OTHER INFORMATION: Primer

<400> SEQUENCE: 104
aggtccccgc ggtcggctag    20

<210> SEQ ID NO 105
<211> LENGTH: 28
<212> TYPE: DNA
<213> ORGANISM: Artificial
<220> FEATURE:
<223> OTHER INFORMATION: Primer

<400> SEQUENCE: 105
agccgaccgc ggggacctgg gcaatgtt    28

<210> SEQ ID NO 106
<211> LENGTH: 216

```
<212> TYPE: DNA
<213> ORGANISM: Triticum aestivum

<400> SEQUENCE: 106
accgatacgg gcgatcatca caaccagaaa actgaatggc ctgaactggt tggtaaaagc      60
gtcgaagagg caaagaaagt aatcctgcaa gacaaatctg aagcgcagat tgttgtactg     120
ccagttggca ccatcgtgac tatggagtac cgtatcgacc gtgttcgtct gttcgttgat    180
tccctggaca aaattgctca ggtgccgcgc gtgggt                              216

<210> SEQ ID NO 107
<211> LENGTH: 216
<212> TYPE: DNA
<213> ORGANISM: Artificial
<220> FEATURE:
<223> OTHER INFORMATION: Protease Inhibitor(B)

<400> SEQUENCE: 107
accgatacgg gcgatcatca caaccagaaa actgattggc ctgaactggt tggtaaaagc      60
gtcgaagagg caaagaaagt aatcctgcaa gacaaatctg aagcgcagat tgctgtactg    120
ccagttggca ccatcgtgac tgcggaggcc gctgccgccc gtgttcgtct gttcgttgat    180
tccctggaca aaattgctca ggtgccggcc gtgggt                              216

<210> SEQ ID NO 108
<211> LENGTH: 255
<212> TYPE: DNA
<213> ORGANISM: Artificial
<220> FEATURE:
<223> OTHER INFORMATION: Synthetic Construct

<400> SEQUENCE: 108
atgagttcag tggagaagaa gccggaggga gtgaacaccg gtgctggtga ccgtcacaac     60
ctgaagacag agtggccaga gttggtgggg aaatcggtgg aggaggccaa gaaggtgatt    120
ctgcaggaca agtcagaggc gcaaatcata gttctgccgg tggggacaat tgtgaccatg    180
gaatatcgga tcgaccgcgt ccgcctcttt gtcgataaac tcgacaacat tgcccaggtc    240
cccagggtcg gctag                                                    255

<210> SEQ ID NO 109
<211> LENGTH: 210
<212> TYPE: DNA
<213> ORGANISM: Artificial
<220> FEATURE:
<223> OTHER INFORMATION: Protease Inhibitor

<400> SEQUENCE: 109
acggagtgcg gcggcggcgg cggcgccaag acgtcgtggc cggaggtggt cgggctgagt     60
gtggaggaag ccaagaaggt gatccttaag gacaagcccg acgccgacat cgtggtgctg    120
cccgtcggct ccgtggtgac cgcggattat cgccctaacc gtgtccgcat cttcgtcgac    180
atcgtcgccc agacgccccca cgtcggctga                                   210
```

PROTEINACEOUS PROTEASE INHIBITOR AND PROTEIN SOLUTION AND DETERGENT COMPOSITION CONTAINING IT

TECHNICAL FIELD

The present invention relates to proteinaceous protease inhibitors, and protein solutions and detergent compositions containing these inhibitors.

BACKGROUND ART

Proteases are a family of enzymes that catalyze the hydrolysis of peptide bonds and are known to exist in a wide variety of microorganisms, animals and plants. They are commonly used in various fields for laundry detergents, automatic dishwashing detergents, contact lens detergents, bath additives, keratolytic cosmetics, food modifiers (e.g. breadmaking, meat tenderization and fish processing), clarifying agents for beer, leather tanning agents, gelatin removing agents for photographic films, digestion promoting preparations and anti-inflammatory preparations, for example.

Unfortunately, proteases hydrolyze themselves and other proteins to remarkably decrease the activities of their own and of the other proteins over time.

Some approaches to inhibiting the hydrolysis of proteases themselves and other proteins focus on protease inhibitors that inhibit protease activity. As examples of protease inhibitors, Streptomyces subtilisin inhibitor (SSI) from Streptomyces species (Non Patent Literature 1) and chymotrypsin inhibitor 2 from barley (Non Patent Literature 2) are mentioned.

Unfortunately, because of their too strong inhibitory activity, most of known naturally occurring protease inhibitors, when used in protease solutions, do not allow the solutions to be reactivated by dilution prior to use.

CITATION LIST

Non Patent Literature

Non Patent Literature 1: Agricultural and Biological Chemistry, 1972, 36, p 160-163
Non Patent Literature 2: Journal of Molecular Biology, 1983, 168, p 445-447

SUMMARY OF INVENTION

Technical Problem

An object of the present invention is to provide proteinaceous protease inhibitors with moderate inhibitory activity. Specifically, an object of the present invention is to provide proteinaceous protease inhibitors that inhibit the activities of proteases and allow the proteases to be reactivated. Another object is to provide protein solutions containing such proteinaceous protease inhibitors which retain protease activity even after long-term storage. A further object is to provide detergent compositions containing such proteinaceous protease inhibitors which retain cleaning performance even after long-term storage.

Solution to Problem

The present inventors studied to achieve the above objects, and thereby completed the present invention.

Specifically, the present invention provides: a protease inhibitor including an amino acid sequence (Y) or an amino acid sequence (Y'), the amino acid sequence (Y) being different from the amino acid sequence (A) of a proteinaceous protease inhibitor (BC), represented by SEQ ID NO:1, by one to eight amino acid replacements with amino acids different from replaced amino acids, the amino acid sequence (Y') having at least 80% homology to the amino acid sequence (Y), wherein the proteinaceous protease inhibitor satisfies at least one of the following conditions (1) to (8); a protein solution containing this proteinaceous protease inhibitor, a protease (D), and a solvent (E); and a detergent composition containing this proteinaceous protease inhibitor, a protease (D), a solvent (E) and a surfactant (F).

(1) The amino acid residue at a position corresponding to residue 12 of the amino acid sequence (A) in the amino acid sequence (Y) or (Y') is an amino acid (X1) defined below.
(2) The amino acid residue at a position corresponding to residue 38 of the amino acid sequence (A) in the amino acid sequence (Y) or (Y') is an amino acid (X2) defined below.
(3) The amino acid residue at a position corresponding to residue 48 of the amino acid sequence (A) in the amino acid sequence (Y) or (Y') is an amino acid (X3) defined below.
(4) The amino acid residue at a position corresponding to residue 50 of the amino acid sequence (A) in the amino acid sequence (Y) or (Y') is an amino acid (X4) defined below.
(5) The amino acid residue at a position corresponding to residue 51 of the amino acid sequence (A) in the amino acid sequence (Y) or (Y') is an amino acid (X5) defined below.
(6) The amino acid residue at a position corresponding to residue 52 of the amino acid sequence (A) in the amino acid sequence (Y) or (Y') is an amino acid (X6) defined below.
(7) The amino acid residue at a position corresponding to residue 53 of the amino acid sequence (A) in the amino acid sequence (Y) or (Y') is an amino acid (X7) defined below.
(8) The amino acid residue at a position corresponding to residue 70 of the amino acid sequence (A) in the amino acid sequence (Y) or (Y') is an amino acid (X8) defined below.
(X1): Any of amino acids (X0) other than Glu
(X2): Any of the amino acids (X0) other than Val and Ile
(X3): Any of the amino acids (X0) other than Met
(X4): Any of the amino acids (X0) other than Tyr
(X5): Any of the amino acids (X0) other than Arg
(X6): Any of the amino acids (X0) other than Ile
(X7): Any of the amino acids (X0) other than Asp
(X8): Any of the amino acids (X0) other than Arg
(X0): Ala, Arg, Asn, Asp, Cys, Gly, Gln, Glu, His, Ile, Leu, Lys, Met, Phe, Pro, Ser, Thr, Trp, Tyr, or Val

Advantageous Effects of Invention

The proteinaceous protease inhibitor of the present invention inhibits the activities of proteases, and allows the proteases to be reactivated by dilution with water or the like.

The protein solution of the present invention retains protease activity even after long-term storage.

The detergent composition of the present invention retains good cleaning performance even after long-term storage.

DESCRIPTION OF EMBODIMENTS

The proteinaceous protease inhibitor of the present invention includes an amino acid sequence (Y) or an amino acid sequence (Y'), the amino acid sequence (Y) being different from the amino acid sequence (A) of a proteinaceous protease inhibitor (BC), represented by SEQ ID NO:1, by one to eight amino acid replacements with amino acids different from replaced amino acids, the amino acid sequence (Y') having at least 80% homology to the amino acid sequence (Y), wherein the proteinaceous protease inhibitor satisfies at least one of the following conditions (1) to (8):

(1) the amino acid residue at a position corresponding to residue 12 of the amino acid sequence (A) in the amino acid sequence (Y) or (Y') is an amino acid (X1) defined below;

(2) the amino acid residue at a position corresponding to residue 38 of the amino acid sequence (A) in the amino acid sequence (Y) or (Y') is an amino acid (X2) defined below;

(3) the amino acid residue at a position corresponding to residue 48 of the amino acid sequence (A) in the amino acid sequence (Y) or (Y') is an amino acid (X3) defined below;

(4) the amino acid residue at a position corresponding to residue 50 of the amino acid sequence (A) in the amino acid sequence (Y) or (Y') is an amino acid (X4) defined below;

(5) the amino acid residue at a position corresponding to residue 51 of the amino acid sequence (A) in the amino acid sequence (Y) or (Y') is an amino acid (X5) defined below;

(6) the amino acid residue at a position corresponding to residue 52 of the amino acid sequence (A) in the amino acid sequence (Y) or (Y') is an amino acid (X6) defined below;

(7) the amino acid residue at a position corresponding to residue 53 of the amino acid sequence (A) in the amino acid sequence (Y) or (Y') is an amino acid (X7) defined below;

(8) the amino acid residue at a position corresponding to residue 70 of the amino acid sequence (A) in the amino acid sequence (Y) or (Y') is an amino acid (X8) defined below:

(X1): any of amino acids (X0) other than Glu
(X2): any of the amino acids (X0) other than Val and Ile
(X3): any of the amino acids (X0) other than Met
(X4): any of the amino acids (X0) other than Tyr
(X5): any of the amino acids (X0) other than Arg
(X6): any of the amino acids (X0) other than Ile
(X7): any of the amino acids (X0) other than Asp
(X8): any of the amino acids (X0) other than Arg; and
(X0): Ala, Arg, Asn, Asp, Cys, Gly, Gln, Glu, His, Ile, Leu, Lys, Met, Phe, Pro, Ser, Thr, Trp, Tyr, or Val.

The proteinaceous protease inhibitor (BC) herein is a protein represented by the amino acid sequence (A) of SEQ ID NO:1, and having the ability to inhibit protease activity. Specifically, the proteinaceous protease inhibitor (BC) is a wheat-derived subtilisin/chymotrypsin inhibitor.

The proteinaceous protease inhibitor of the present invention that includes an amino acid sequence (Y) or an amino acid sequence (Y'), the amino acid sequence (Y) being different from the amino acid sequence (A) of a proteinaceous protease inhibitor (BC), represented by SEQ ID NO:1, by one to eight amino acid replacements with amino acids different from the replaced amino acids, the amino acid sequence (Y') having at least 80% homology to the amino acid sequence (Y), wherein the proteinaceous protease inhibitor satisfies at least one of the above-mentioned conditions (1) to (8).

The position corresponding to residue 12 of the amino acid sequence (A) specified in the condition (1) is intended to include residue 12 of the amino acid sequence (A) and positions determined to correspond to residue 12 of the amino acid sequence (A) by a below-mentioned homology analysis program. The amino acid (X1) is any of the amino acids (X0) other than Glu, and is preferably Asp, Ala, Asn, Gln, Leu, Lys, Ser, Thr, or Val, more preferably Asp, Ala, Asn, Gln, or Lys, particularly preferably Ala, Asp, or Lys in terms of moderate inhibitory effects on protease activity and ease of reactivation of proteases by dilution.

The position corresponding to residue 38 of the amino acid sequence (A) specified in the condition (2) is intended to include residue 38 of the amino acid sequence (A) and positions determined to correspond to residue 38 of the amino acid sequence (A) by the below-mentioned homology analysis program. The amino acid (X2) is any of the amino acids (X0) other than Val and Ile, and is preferably Ala, Gly, Leu, Phe, Ser, Thr, or Trp, more preferably Ala or Leu, particularly preferably Ala in terms of moderate inhibitory effects on protease activity and ease of reactivation of proteases by dilution.

The position corresponding to residue 48 of the amino acid sequence (A) specified in the condition (3) is intended to include residue 48 of the amino acid sequence (A) and positions determined to correspond to residue 48 of the amino acid sequence (A) by the below-mentioned homology analysis program. The amino acid (X3) is any of the amino acids (X0) other than Met, and is preferably Ala, Ile, Leu, Ser, Thr, Gly, or Val, more preferably Ala, Leu, Ser, Gly, or Val, particularly preferably Ala or Gly in terms of moderate inhibitory effects on protease activity and ease of reactivation of proteases by dilution.

The position corresponding to residue 50 of the amino acid sequence (A) specified in the condition (4) is intended to include residue 50 of the amino acid sequence (A) and positions determined to correspond to residue 50 of the amino acid sequence (A) by the below-mentioned homology analysis program. The amino acid (X4) is any of the amino acids (X0) other than Tyr, and is preferably Ala, Phe, Gly, Ile, Leu, Ser, Thr, or Val, more preferably Ala, Phe, or Leu in terms of moderate inhibitory effects on protease activity and ease of reactivation of proteases by dilution.

The position corresponding to residue 51 of the amino acid sequence (A) specified in the condition (5) is intended to include residue 51 of the amino acid sequence (A) and positions determined to correspond to residue 51 of the amino acid sequence (A) by the below-mentioned homology analysis program. The amino acid (X5) is any of the amino acids (X0) other than Arg, and is preferably Ala, Lys, His, Ile, Leu, Ser, Thr, or Val, more preferably Ala, Lys, or His in terms of moderate inhibitory effects on protease activity and ease of reactivation of proteases by dilution.

The position corresponding to residue 52 of the amino acid sequence (A) specified in the condition (6) is intended to include residue 52 of the amino acid sequence (A) and positions determined to correspond to residue 52 of the amino acid sequence (A) by the below-mentioned homology analysis program. The amino acid (X6) is any of the amino acids (X0) other than Ile, and is preferably Glu, Ala, Asn, Gln, Leu, Ser, Thr, or Val, more preferably Ala, Val, or Gln, particularly preferably Ala or Val in terms of moderate inhibitory effects on protease activity and ease of reactivation of proteases by dilution.

The position corresponding to residue 53 of the amino acid sequence (A) specified in the condition (7) is intended to include residue 53 of the amino acid sequence (A) and positions determined to correspond to residue 53 of the amino acid sequence (A) by the below-mentioned homology analysis program. The amino acid (X7) is any of the amino acids (X0) other than Asp, and is preferably Glu, Ala, Asn, Gln, Ile, Leu, Ser, Thr, or Val, more preferably Glu, Ala, Asn, or Gln, particularly preferably Glu or Ala in terms of moderate inhibitory effects on protease activity and ease of reactivation of proteases by dilution.

The position corresponding to residue 70 of the amino acid sequence (A) specified in the condition (8) is intended to include residue 70 of the amino acid sequence (A) and positions determined to correspond to residue 70 of the amino acid sequence (A) by the below-mentioned homology analysis program. The amino acid (X8) is any of the amino acids (X0) other than Arg, and is preferably Ala, Asn, Lys, His, Ile, Leu, Ser, Gly, Thr, or Val, more preferably Ala, Asn, Gly, Lys, Ile, or Leu, particularly preferably Ala, Asn, Gly, or Lys in terms of moderate inhibitory effects on protease activity and ease of reactivation of proteases by dilution.

The one to eight amino acid replacements in the amino acid sequence of SEQ ID NO:1 with amino acids different from the replaced amino acids to create the proteinaceous protease inhibitor of the present invention result in effects of the proteinaceous protease inhibitor of moderately inhibiting protease activity and allowing for reactivation of proteases by dilution.

Because of its moderate inhibitory effects on protease activity, the proteinaceous protease inhibitor of the present invention moderately inhibits the hydrolysis of proteases, and therefore enables high levels of retained protease activity to be achieved.

The "retained protease activity" herein means that a sample retains a certain level of protease activity, specifically that when a sample is diluted and measured for protease activity immediately before and after storage for a certain period, the change in the protease activity is small, in other words, the protease activity ratio (%) {(protease activity measured after storage for a certain period)/(protease activity measured immediately before storage)×100} is close to 100%.

The proteinaceous protease inhibitor of the present invention includes an amino acid sequence (Y) that is different from the amino acid sequence (A) by one to eight amino acid replacements with amino acids different from the replaced amino acids, or an amino acid sequence (Y') having at least 80% homology to the amino acid sequence (Y). The number of substituted amino acid(s) in the amino acid sequence (Y) or (Y') is preferably 1 to 5, more preferably 1 to 3 in terms of moderate inhibitory effects on protease activity and ease of reactivation of proteases by dilution.

The proteinaceous protease inhibitor of the present invention includes at least one copy of the amino acid sequence (Y) or (Y'), and preferably include 1 to 4 copies in terms of moderate inhibitory effects on protease activity and ease of reactivation of proteases by dilution.

The proteinaceous protease inhibitor of the present invention, which includes the amino acid sequence (Y) or (Y'), may consist only of the amino acid sequence (Y) or (Y'), or may include an amino acid sequence in which one or more copies of an amino acid sequence (Z) are present on the C terminal side and/or the N terminal side of the amino acid sequence (Y) or (Y'). Alternatively, the proteinaceous protease inhibitor of the present invention may include repeating copies of these sequences.

The amino acid sequence (Z) is a peptide sequence consisting of one amino acid or two or more amino acids bonded together.

The number of amino acids in the amino acid sequence (Z) is preferably 1 to 100, more preferably 1 to 50 in terms of moderate inhibitory effects on protease activity and ease of reactivation of proteases by dilution.

In the case where the proteinaceous protease inhibitor of the present invention includes the amino acid sequence (Z), the number of copies of the amino acid sequence (Z) is preferably 1 to 100 in terms of moderate inhibitory effects on protease activity and ease of reactivation of proteases by dilution.

The proteinaceous protease inhibitor of the present invention preferably includes 1 to 100, more preferably 1 to 50 additional amino acids besides the amino acid sequence (Y) or (Y') in its amino acid sequence in terms of moderate inhibitory effects on protease activity and ease of reactivation of proteases by dilution.

Proteinaceous protease inhibitors (B) including the amino acid sequence (Y) and proteinaceous protease inhibitors (C) including the amino acid sequence (Y') are included within the scope of the proteinaceous protease inhibitor of the present invention.

Specific examples of the proteinaceous protease inhibitors (B), which are proteinaceous protease inhibitors including the amino acid sequence (Y), include proteinaceous protease inhibitors represented by SEQ ID NOs:2 to 29 and 37 to 39.

Among the inhibitors (B), those represented by SEQ ID NO:2 to 29 and 37 to 39 are preferred in terms of moderate inhibitory effects on protease activity and ease of reactivation of proteases by dilution. More preferred are those represented by SEQ ID NOs:2 to 11 and 14 to 29, and particularly preferred are those represented by SEQ ID NOs:3, 4, 10, 11, 14 to 19, 22, 23 and 25. In terms of the retained protease activity, those represented by SEQ ID NO:2 to 4, 10 to 23 and 25 are preferred, and those represented by SEQ ID NO:4, 12, 14, 15, 18, 19, 22, 23 and 25 are more preferred.

The inhibitors (B) are intended to include proteinaceous protease inhibitors (B-1) extracted from natural products, and proteinaceous protease inhibitors (B-2) produced by recombinant techniques.

The proteinaceous protease inhibitors (B-1) extracted from natural products are intended to include proteinaceous protease inhibitors including the amino acid sequence (Y) which can be extracted from natural products (e.g. plant cells, animal cells, extracellular tissues, seeds, intracellular or extracellular secretions of microorganisms).

The extraction can be accomplished by common techniques for separating proteins from natural products, such as disruption of cell walls and cell membranes, centrifugation, ammonium sulfate fractionation, chromatography and dialysis.

The amino acid sequence of the inhibitors (B-1) can be determined by common techniques, such as peptide mapping.

Whether a protein extracted from a natural product is included within the scope of the inhibitors (B-1) can be determined by determining the amino acid sequence of the extracted protein by common techniques, such as peptide mapping, and searching similar sequences by the blastp algorithm of the homology search program "BLAST" available from National Center for Biotechnology Information (http://blast.ncbi.nlm.nih.gov/Blast.cgi).

Examples of proteinaceous protease inhibitors (B-2) produced by hosts include those recovered from cultures of recombinant hosts that are produced by transfecting suitable hosts with recombinant genes obtained by the recombinant technique described in Japanese Patent No. 3338441. Specifically, such a protein can be produced by cloning a DNA sequence including a DNA sequence encoding the protein having the amino acid sequence of SEQ ID NO:1, partially replacing the cloned DNA sequence with a DNA encoding an amino acid sequence that satisfies at least one of the conditions (1) to (8) (hereinafter, also referred to as "mutagenesis"), transfecting the mutated DNA into a suitable host, culturing the recombinant host, and recovering the target protein from the culture.

The cloning of a DNA can be accomplished by common DNA recombinant techniques, for example, using cDNA libraries or artificial synthetic genes. The mutagenesis can be accomplished by common site-specific mutagenesis methods, specifically by using Agilent Technologies' Quick Change Site-Directed Mutagenesis Kit, for example.

In the case that such a mutated gene is used to produce an inhibitor (B-2), the mutated DNA is incorporated into any suitable vector for expression of the gene in a desired host, and this recombinant vector is transfected into the host to provide a transformant containing the recombinant vector. The transformant is cultured, and the inhibitor (B-2) can be recovered from the culture.

In the present invention, such a recombinant vector can be produced by transfecting the mutated gene into a suitable vector.

Various vectors are known, and many vectors are commercially available. Those skilled in the art should be readily able to determine a vector suitable for a host used. Specific examples of vectors include vectors of pET series and pUC series.

How to construct recombinant vectors is commonly well understood in the art. As specific examples of methods for inserting a mutated gene into a suitable vector and transfecting a host with the vector, mention may be made of electroporation and calcium transformation.

Examples of hosts usable in the present invention include animal cells, microorganisms, and plant cells.

Examples of animal cells include, but are not particularly limited to, insect cells, monkey COS-7 cells, Vero cells, mouse L cells, rat GH3 cells, human FL cells and CHO cells.

Examples of insect cells include, but are not particularly limited to, Sf9 cells and Sf21 cells.

Examples of microorganisms include, but are not particularly limited to, bacteria and yeasts.

The term "bacteria" is intended to include bacteria (eubacterium) and archaea.

Examples of bacteria (eubacterium) include gram-negative bacteria and gram-positive bacteria. Examples of gram-negative bacteria include bacteria of the following genera: *Escherichia; Thermus; Rhizobium; Pseudomonas; Shewanella; Vibrio; Salmonella; Acetobacter*; and *Synechocystis*. Examples of gram-positive bacteria include bacteria of the following genera: *Bacillus; Streptmyces; Corynebacterium; Brevibacillus; Bifidobacterium; Lactococcus; Enterococcus; Pediococcus; Leuconostoc;* and *Streptomyces*.

Examples of plant cells include, but are not particularly limited to, BY-2 cells.

In the present invention, microorganism hosts are preferred in terms of ease of cloning. More preferred are bacteria of *Escherichia, Thermus, Rhizobium, Pseudomonas, Shewanella, Vibrio, Salmonella, Acetobacter, Synechocystis, Bacillus*, and *Brevibacillus*, and particularly preferred are bacteria of *Escherichia, Shewanella, Bacillus*, and *Brevibacillus*.

The culturing can be accomplished by inoculating a microorganism into a medium containing carbon sources, nitrogen sources and other nutritional components which the microorganism is able to utilize, and culturing the microorganism by common methods.

In the present invention, the recovery and purification of inhibitors (B-2) from cultures can be accomplished by common methods. For example, a culture is centrifuged or filtered to remove cells therein and a desired enzyme is concentrated from the obtained supernatant of the culture by common techniques. A solution or dry powder of the enzyme thus obtained may be used as is, or may be crystallized or granulated by known techniques.

The inhibitors (C) herein are intended to include inhibitors including the amino acid sequence (Y') having at least 80% homology to the amino acid sequence (Y). The homology between the amino acid sequence (Y) and the amino acid sequence (Y') is preferably not lower than 90%, more preferably not lower than 95%, most preferably not lower than 97% in terms of moderate inhibitory effects on protease activity and ease of reactivation of proteases by dilution.

The homology between amino acid sequences is analyzed using the blastp algorithm of the homology search program "BLAST" available from National Center for Biotechnology Information (http://blast.ncbi.nlm.nih.gov/Blast.cgi).

Specific examples of the proteinaceous protease inhibitor (C), which includes the amino acid sequence (Y') having at least 80% homology to the amino acid sequence (Y), include proteinaceous protease inhibitors of SEQ ID NOs:30 to 36.

Among the inhibitors (C), proteinaceous protease inhibitors of SEQ ID NOs:30 to 32 and 34 to 36 are preferred in terms of moderate inhibitory effects on protease activity and ease of reactivation of proteases by dilution. In terms of the retained protease activity, proteinaceous protease inhibitors of SEQ ID NO:31 and 33 to 36 are preferred among the inhibitors (C).

The inhibitors (C) are intended to include proteinaceous protease inhibitors (C-1) extracted from natural products, and host-produced proteinaceous protease inhibitors (C-2).

The proteinaceous protease inhibitors (C-1) extracted from natural products are intended to include proteinaceous protease inhibitors having the amino acid sequence (Y') having at least 80% homology to the amino acid sequence of inhibitors (B) which satisfy at least one of the following conditions (1) to (8), and can be extracted from natural products (e.g. plant cells, animal cells, extracellular tissues, seeds, intracellular or extracellular secretions of microorganisms).

The extraction can be accomplished by common techniques for separating proteins from natural products, such as disruption of cell walls and cell membranes, centrifugation, ammonium sulfate fractionation, chromatography and dialysis.

The amino acid sequence of the inhibitors (C-1) can be determined by common techniques, such as peptide mapping.

Whether a protein extracted from a natural product is included within the scope of the inhibitors (C-1) can be determined by determining whether the extracted protein has at least 80% homology as follows: determining the amino acid sequence of the extracted protein by common techniques, such as peptide mapping; searching a sequence corresponding to that of an inhibitor (B) using the sequence comparison program "ClustalW" (http://clustalw.ddbj.nig.ac.jp/top-j.html) from DNA Data Bank of Japan; and determining the homology of the similar sequence to the sequence of the inhibitor (B) by the blastp algorithm of the homology search program "BLAST" available from National Center for Biotechnology Information (http://blast.ncbi.nlm.nih.gov/Blast.cgi).

Examples of proteinaceous protease inhibitors (C-2) produced by hosts include those recovered from cultures of recombinant hosts that are produced by transfecting suitable hosts with recombinant genes obtained by the recombinant technique described in Japanese Patent No. 3338441.

Specifically, such a protein can be produced by cloning a DNA sequence encoding an amino acid sequence having at least 80% homology to the amino acid sequence of an inhibitor (B) or an amino acid sequence that has at least 80% homology to the amino acid sequence of an inhibitor (B) as determined excluding the sites specified in the conditions (1) to (8), partially replacing the cloned DNA sequence with a DNA encoding an amino acid sequence that satisfies at least one of the conditions (1) to (8), transfecting the mutated DNA into a suitable host, culturing the recombinant host, and recovering the target protein from the culture.

The cloning of a DNA can be accomplished by common DNA recombinant techniques, for example, using cDNA libraries or artificial synthetic genes. The mutagenesis can be accomplished by common site-specific mutagenesis methods, specifically by using Agilent Technologies' Quick Change Site-Directed Mutagenesis Kit, for example.

In the case that such a mutated gene is used to produce an inhibitor (C-2), the mutated DNA is incorporated into any suitable vector for expression of the gene in a desired host, and this recombinant vector is transfected into the host to provide a transformant containing the recombinant vector. The transformant is cultured, and the inhibitor (C-2) can be recovered from the culture.

In the present invention, such a recombinant vector can be produced by transfecting the mutated gene into a suitable vector. Specific examples of vectors include the same vectors mentioned for the inhibitors (B-2).

Preferred hosts are also the same as those mentioned for the inhibitors (B-2).

The culturing can be accomplished by inoculating a microorganism into a medium containing carbon sources, nitrogen sources and other nutritional components which the microorganism is able to utilize, and culturing the microorganism by common methods.

In the present invention, the recovery and purification of inhibitors (C-2) from cultures can be accomplished by common methods. For example, a culture is centrifuged or filtered to remove cells therein and a desired enzyme is concentrated from the obtained supernatant of the culture by common techniques. A solution or dry powder of the enzyme thus obtained may be used as is, or may be crystallized or granulated by known techniques.

The proteinaceous protease inhibitors (B) and (C) of the present invention can be used in the same manner as known protease inhibitors.

The proteinaceous protease inhibitors (B) and (C) of the present invention are useful as additives for protease storage, laundry detergents, dishwashing detergents, fiber treating agents, and food modifiers because they inhibit the activities of proteases, and allow the proteases to be reactivated by dilution.

The protein solution of the present invention contains the proteinaceous protease inhibitor, a protease (D) and a solvent (E).

The proteinaceous protease inhibitor in the protein solution of the present invention is any of the inhibitors (B) and (C).

The protein solution preferably contains the proteinaceous protease inhibitor in an amount of 0.000001 to 50% by weight, more preferably 0.00005 to 30% by weight, particularly preferably 0.0001 to 20% by weight of the protein solution in terms of moderate inhibitory effects on the protease activity and ease of reactivation of proteases by dilution.

The protease (D) may be any of common proteases, and mention may be made of low-temperature proteases, the protease activity of which has an optimal temperature within a low temperature range (0 to 50° C.), and high-temperature proteases, the protease activity of which has an optimal temperature within a high temperature range (higher than 50° C.). The protease (D) is preferably a serine protease, and more preferably subtilisin in terms of desired activity. Examples of commercial products include Alcalase, Savinase, Everlase, and PTN (all from Novozymes), and Purafect and Purafect OXP (both from Genencor).

The protein solution preferably contains the protease (D) in an amount of 0.001 to 10% by weight, more preferably 0.005 to 5% by weight, particularly preferably 0.01 to 2% by weight of the protein solution in terms of the ability to decompose proteins.

The proteinaceous protease inhibitor and the protease (D) are present in the protein solution at a ratio (proteinaceous protease inhibitor/(D)) on a molar basis of 1 to 1000, more preferably 1 to 100 in terms of moderate inhibitory effects on the protease activity and ease of reactivation of proteases by dilution.

Examples of the solvent (E) include water, hydrophilic solvents (e.g. methanol, ethanol, isopropyl alcohol, ethyleneglycol, diethyleneglycol and propyleneglycol) and mixtures of these. Examples of water include, but are not particularly limited to, tap water, deionized water, distilled water, and reverse osmosis water. Further examples include buffer aqueous solutions containing a pH adjusting agent in water.

The pH adjusting agent may be any of known pH adjusting agents, and mention may be made of, for example, borate buffers, phosphate buffers, acetate buffers, Tris buffers, HEPES buffers, sulfuric acid, hydrochloric acid, citric acid, lactic acid, pyruvic acid, formic acid, sodium chloride, potassium chloride, monoethanolamine and diethanolamine.

The protein solution contains the solvent (E) preferably in an amount of 40 to 99.9989999% by weight, more preferably 65 to 99.99495% by weight, particularly preferably 78 to 99.9899% by weight of the protein solution in terms of the stability of the protease and the proteinaceous protease inhibitor.

The protein solution of the present invention may further contain a surfactant (F), a salt (G), a sugar (H), an amino acid (I), a fatty acid (Q), an oil/fat (N), and other low-molecular-weight organic compounds (J), and a protein (M) other than proteases, in addition to the proteinaceous protease inhibitor, the protease (D) and the solvent (E).

Examples of the surfactant (F) include the same surfactants as those mentioned below for the surfactant (F) which is an essential component of the later-described detergent composition. As preferred examples, the same surfactants may also be mentioned.

Examples of the salt (G) include inorganic salts (e.g. sodium chloride, sodium borate, calcium chloride, magnesium chloride, magnesium sulfate and ammonium sulfate) and organic salts (sodium formate).

Examples of the sugar (H) include trehalose, sucrose, dextrin, cyclodextrin, maltose, fructose, hyaluronic acid and chondroitin sulfate.

Examples of the amino acid (I) include glycine, alanine, arginine, aspartic acid, asparagine, phenylalanine, tryptophan, tyrosine, leucine, lysine, histidine, cystein, glutamine, glutamic acid, isoleucine, methionine, proline, serine, threonine, valine and salts of these.

Examples of the fatty acid (Q) include oleic acid, linoleic acid, linolenic acid, docosahexaenoic acid and eicosapentaenoic acid.

Examples of the oil/fat (N) include the monoglyceride, diglyceride and triglyceride of the fatty acid (Q).

Examples of the other low-molecular-weight organic compounds (J) include benzyl acetate, methyl salicylate, benzyl salicylate, hydroxybenzoic acid, cinnamic acid, coffeic acid, catechins, ascorbic acid and carotenoids.

Examples of the protein (M) other than proteases include, but are not particularly limited to, enzymes other than proteases, recombinant proteins, antibodies and peptides, and specifically mention may be made of, for example, cellulase, serum albumin, collagen, casein, gelatin and silk peptides.

The protein solution of the present invention preferably contains the surfactant (F) in an amount of 0 to 90% by weight, more preferably 0 to 85% by weight, particularly preferably 0 to 80% by weight of the protein solution in terms of the stability of the proteins.

The protein solution of the present invention preferably contains the salt (G) in an amount of 0 to 10% by weight, more preferably 0 to 5% by weight, particularly preferably 0 to 3% by weight of the protein solution in terms of the stability of the proteins.

The protein solution of the present invention preferably contains the sugar (H) in an amount of 0 to 50% by weight, more preferably 0 to 30% by weight, particularly preferably 0 to 20% by weight of the protein solution in terms of the stability of the proteins.

The protein solution of the present invention preferably contains the amino acid (I) in an amount of 0 to 50% by weight, more preferably 0 to 30% by weight, particularly preferably 0 to 20% by weight of the protein solution in terms of the stability of the proteins.

The protein solution of the present invention preferably contains other low-molecular-weight organic compounds (J) in an amount of 0 to 50% by weight, more preferably 0 to 30% by weight, particularly preferably 0 to 20% by weight of the protein solution in terms of the stability of the proteins.

The protein solution of the present invention preferably contains the fatty acid (Q) in an amount of 0 to 50% by weight, more preferably 0 to 30% by weight, particularly preferably 0 to 20% by weight of the protein solution in terms of the stability of the proteins.

The protein solution of the present invention preferably contains the oil/fat (N) in an amount of 0 to 50% by weight, more preferably 0 to 30% by weight, particularly preferably 0 to 20% by weight of the protein solution in terms of the stability of the proteins.

The protein solution of the present invention preferably contains the protein (M) other than proteases in an amount of 0 to 50% by weight, more preferably 0 to 30% by weight, particularly preferably 0 to 20% by weight of the protein solution in terms of the stability of the proteins.

The remaining activity of the protein solution of the present invention, which is a measure of the activity of the protease in the protein solution, is preferably not more than 10% in terms of moderate inhibition of the protease activity.

The remaining activity can be determined as follows.

<How to Measure Remaining Activity>

The protein solution containing certain amounts of the protease (D), the proteinaceous protease inhibitor and the solvent (E) is mixed with a substrate solution (e.g. an aqueous solution containing casein, azocasein or benzoyl arginine ethyl ester) to provide a solution (i).

The solution (i) should be kept at a temperature within the range of 20 to 70° C. in which the protease (D) is not deactivated, and shows enough activity to allow for the measurement of absorbance. During the measurement, the temperature is kept constant.

The molar concentration of the substrate in the solution (i) is ⅓- to 2-fold of the Michaelis constant $K_m$, and 5- to 100,000-fold of the molar concentration of the protease (D) in the solution (i). The Michaelis constant refers to the Michaelis constant of the substrate-protease reaction, and is determined as the dependence of the initial velocity on the substrate concentration in the enzymatic reaction by the method disclosed by Agarwal et al. (Methods of enzymology, 1978, Vol. 51, P 483-491).

The solution (i) is measured with a spectrophotometer over time for absorbance $A_\lambda$ at a wavelength within 300 to 450 nm at which a product of the decomposition of the substrate by the protease shows the maximum absorbance. The measurement is performed at the same temperature as the preparation of the solution (i). The solution (i) is measured for absorbance $A_{\lambda,0}$ immediately after preparation thereof and absorbance $A_{\lambda,h}$ after h hours from the preparation to calculate the change in the absorbance $\Delta A_\lambda$ ($\Delta A_\lambda = A_{\lambda,h} - A_{\lambda,0}$). Although depending on the enzyme activity, the duration of the measurement is determined such that the solution shows a change in the absorbance of 0.1 or larger but not larger than 0.8. The change in the absorbance $\Delta A_h$ is plotted along the vertical axis against the time h along the horizontal axis to determine the slope of a drawn line (coefficient $v_1$).

A protein solution in which the proteinaceous protease inhibitor in the above-mentioned protein solution is replaced by the same amount of the solvent (E) is mixed with the substrate solution under the same conditions for the solution (i) to provide a solution (ii).

As for the solution (ii), the change in the absorbance $\Delta A_\lambda$ is likewise plotted along the vertical axis against the time h along the horizontal axis to determine the slope of a drawn line (coefficient $v_0$). The obtained values are substituted into the following formula (1) to determine the remaining activity.

$$\text{Remaining activity (\%)} = v_1/v_0 \times 100 \tag{1}$$

The detergent composition of the present invention contains the proteinaceous protease inhibitor, the protease (D), the solvent (E) and a surfactant (F). The presence of the proteinaceous protease inhibitor enables good cleaning performance to be retained even after long-term storage.

The proteinaceous protease inhibitor in the detergent composition of the present invention is any of the inhibitors (B) and (C). Preferred examples of the proteinaceous protease inhibitor in the detergent composition are the same as those mentioned as preferred examples of the inhibitors (B) and (C).

The detergent composition preferably contains the proteinaceous protease inhibitor in an amount of 0.000001 to 50% by weight, more preferably 0.00005 to 20% by weight, particularly preferably 0.0001 to 10% by weight of the detergent composition in terms of moderate inhibitory effects on the protease activity and ease of reactivation of proteases by dilution. The presence of the inhibitor in an amount within this range ensures efficient inhibition of the protease during storage, and improved cleaning performance for washing.

The protease (D) may be any of known proteases as described for the protease in the protein solution. Preferred is serine protease, and more preferred is subtilisin. Examples of commercial products include Alcalase, Savinase, Everlase, and PTN (all from Novozymes), and Purafect and Purafect OXP (both from Genencor).

The detergent composition preferably contains the protease (D) in an amount of 0.001 to 10% by weight, more preferably 0.005 to 3% by weight, particularly preferably 0.01 to 1% by weight of the detergent composition in terms of the cleaning performance.

The proteinaceous protease inhibitor and the protease (D) are present in the detergent composition at a ratio (proteinaceous protease inhibitor/(D)) on a molar basis of 1 to 1000, more preferably 1 to 100 in terms of the cleaning performance.

Examples of the solvent (E) include those mentioned for the solvent (E) in the protein solution, such as water, hydrophilic solvents (e.g. methanol, ethanol, isopropyl alcohol, ethyleneglycol, diethyleneglycol and propyleneglycol) and mixtures of these. Examples of water include, but are not particularly limited to, tap water, deionized water, distilled water, and reverse osmosis water. Further examples include buffer aqueous solutions containing a pH adjusting agent in water.

The pH adjusting agent may be any of known pH adjusting agents, and mention may be made of, for example, borate buffers, phosphate buffers, acetate buffers, Tris buffers, HEPES buffers, sulfuric acid, hydrochloric acid, citric acid, lactic acid, pyruvic acid, formic acid, sodium chloride, potassium chloride, monoethanolamine and diethanolamine.

The detergent composition preferably contains the solvent (E) in an amount of 1 to 95% by weight, more preferably 17 to 90% by weight, particularly preferably 29 to 80% by weight of the detergent composition in terms of the stability of the protease and the proteinaceous protease inhibitor.

Examples of the surfactant (F) include nonionic surfactants (F-1), anionic surfactants (F-2), cationic surfactants (F-3) and amphoteric surfactants (F-4).

Examples of the nonionic surfactants (F-1) include alkylene oxide-adduct-type nonionic surfactants (F-1-1) and polyhydric alcohol-type nonionic surfactants (F-1-2).

Examples of the surfactants (F-1-1) include aliphatic alcohol (C8 to C24)-alkylene (C2 to C4, preferably C2) oxide adducts (number of moles of addition: 1 to 100 per active hydrogen), alkyl (01 to C18) phenol-ethylene oxide (hereinafter, abbreviated as EO) adducts (number of moles of addition: 1 to 100), higher amine (C8 to C24)-alkylene (C2 to C4, preferably C2) oxide adducts (number of moles of addition: 1 to 100 per active hydrogen), fatty acid (C8 to 024)-EO adducts (number of moles of addition: 1 to 100 per active hydrogen), polypropylene glycol (molecular weight: 200 to 4000)-EO adducts (number of moles of addition: 1 to 100 per active hydrogen), polyoxyethylene (degree of polymerization=3 to 30) alkyl (C6 to C20) allylethers, and EO adducts of fatty acid (C8 to C24) esters of polyhydric (di- to octahydric or higher polyhydric) alcohols (C2 to 30) (number of moles of addition: 1 to 100 per active hydrogen) (e.g. sorbitan monolaurate-EO adducts (number of moles of addition: 1 to 100 per active hydrogen) and sorbitan monooleate-EO adducts (number of moles of addition: 1 to 100 per active hydrogen)).

Examples of the surfactants (F-1-2) include fatty acid (C8 to C24) esters of polyhydric (di- to octahydric or higher polyhydric) alcohols (C2 to 30), such as glycerin monostearate, glycerin monooleate, sorbitan monolaurate and sorbitan monooleate, and fatty acid alkanolamides, such as lauric acid monoethanolamide and lauric acid diethanolamide.

Examples of the anionic surfactants (F-2) include alkyl (C8 to C24) ether carboxylic acids or salts thereof and (poly) oxyethylene alkyl (C8 to C24) ether carboxylic acids or salts thereof [e.g. (poly)oxyethylene (degree of polymerization=1 to 100) lauryl ether sodium acetate and (poly)oxyethylene (degree of polymerization=1 to 100) disodium lauryl sulfosuccinate]; salts of alkyl (C8 to C24) sulfate esters, salts of (poly)oxyethylene alkyl (C8 to C24) sulfate esters [e.g. sodium lauryl sulfate, sodium (poly)oxyethylene (degree of polymerization=1 to 100) lauryl sulfate, and (poly)oxyethylene (degree of polymerization=1 to 100) lauryl sulfate triethanolamine salts]; coconut oil fatty acid monoethanolamide sodium sulfate; alkyl (C8 to C24) phenyl sulfonate salts [e.g. sodium dodecyl benzene sulfonate]; alkyl (C8 to C24) phosphate ester salts and (poly)oxyethylene alkyl (C8 to C24) phosphate ester salts [e.g. sodium lauryl phosphate and (poly) oxyethylene (degree of polymerization=1 to 100) sodium lauryl ether phosphate]; fatty acid salts [e.g. sodium laurate and triethanolamine laurate]; acylated amino acid salts [e.g. coconut oil fatty acid methyl taurine sodium, coconut oil fatty acid sarcosine sodium, coconut oil fatty acid sarcosine triethanolamine, N-coconut oil fatty acid acyl-L-glutamic acid triethanolamine, N-coconut oil fatty acid acyl-sodium L-glutamate, and lauroyl methyl-β-alanine sodium].

Examples of the cationic surfactants (F-3) include quaternary ammonium salts [e.g. stearyl trimethyl ammonium chloride, behenyl trimethyl ammonium chloride, distearyl dimethyl ammonium chloride, and lanolin fatty acid aminopropyl ethyl dimethyl ammonium ethyl sulfate] and amine salts [e.g. stearic diethylaminoethylamide lactate, dilaurylamine hydrochloride, and oleylamine lactate].

Examples of the amphoteric surfactants (F-4) include betaine amphoteric surfactants [e.g. coconut oil fatty acid amidopropyldimethylaminoacetic acid betaine, lauryldimethylaminoacetic acid betaine, 2-alkyl-N-carboxymethyl-N-hydroxyethylimidazolinium betaine, lauryl hydroxyl sulfobetaine, and sodium lauroyl amidoethyl hydroxyethyl carboxymethyl betaine hydroxypropyl phosphate] and amino acid amphoteric surfactants [e.g. sodium β-lauryl aminopropionate].

One or more surfactants (F) can be used. In the case of two or more surfactants being used, nonionic surfactant(s) and anionic surfactant(s), nonionic surfactant(s) and cationic surfactant(s), or nonionic surfactant(s) and amphoteric surfactant(s) can be used in combination, for example.

In terms of the cleaning performance, a nonionic surfactant is preferably used alone, or the combination of a nonionic surfactant and an anionic surfactant is preferably used.

Among the nonionic surfactants (F-1), EO adducts (number of moles of addition: 1 to 100) of aliphatic alcohols (C8 to C24) are preferable in terms of the cleaning performance, EO adducts (number of moles of addition: 4 to 20) of aliphatic alcohols (C12 to C18) are more preferable, EO adducts (number of moles of addition: 8 to C12) of aliphatic alcohols (C12 to C15) are still more preferable, and 11 mole EO adduct of oleylalcohol is particularly preferable.

Among the anionic surfactants (F-2), alkyl (C8 to C24) phenyl sulfonate salts, fatty acid salts, salts of alkyl (C8 to C24) sulfate esters, and salts of (poly)oxyethylene alkyl (C8 to C24) sulfate esters are preferable in terms of the cleaning performance. Alkyl (C12 to C16) phenyl sulfonate salts and fatty acid salts (C8 to C16) are more preferable, and monoethanolamine dodecylbenzene sulfonate and sodium laurate are also preferable.

The detergent composition preferably contains the surfactant (F) in an amount of 1 to 70% by weight, more preferably 5 to 60% by weight, particularly preferably 10 to 60% by weight of the detergent composition in terms of the cleaning performance.

The detergent composition may optionally contain other known components, such as detergent builders, chelating agents, antifoamers, fluorescence whitening agents, bleaching agents, softeners, sterilization agents, aromatics, and colorants disclosed in JP 2004-27181 A.

Examples of detergent builders include polycarboxylic acid salts (e.g. homopolymers of acrylic acid salts and homopolymers of maleic acid salts), salts of polycarboxylic acids (e.g. citric acid and malic acid), and alkaline detergent builders (e.g. sodium hydroxide, soda ash, ammonia, triethanolamine, sodium tripolyphosphate and sodium silicate). Examples of chelating agents include EDTA and NTA. Examples of antifoamers include silicone antifoamers, polyoxyalkylene antifoamers, and mineral oil antifoamers.

The total amount, on a weight basis, of detergent builders and chelating agents, among other components, is preferably not more than 10%, more preferably not more than 5% of the total weight of the detergent composition including the detergent builders and the chelating agents.

The total amount, on a weight basis, of fluorescence whitening agents, bleaching agents, softeners, sterilization agents, aromatics, colorants, and antifoamers is preferably not more than 5%, more preferably not more than 2% of the total weight of the detergent composition including the fluorescence whitening agents, the bleaching agents, the softeners, the sterilization agents, the aromatics, colorants, and the antifoamers.

The detergent composition may optionally contain a salt (G), a sugar (H), an amino acid (I), a fatty acid (Q), an oil/fat (N), and other low-molecular-weight organic compounds (J), and a protein (M) other than proteases, in addition to the above-mentioned components.

Examples of the salt (G), the sugar (H), the amino acid (I), the other low-molecular-weight organic compounds (J), the fatty acid (Q), the oil/fat (N) and the protein (M) other than proteases include those mentioned above as examples of components usable for the protein solution.

The detergent composition of the present invention preferably contains the salt (G) in an amount of 0 to 10% by weight, more preferably 0 to 5% by weight, particularly preferably 0 to 3% by weight of the detergent composition in terms of the cleaning performance.

The detergent composition of the present invention preferably contains the sugar (H) in an amount of 0 to 50% by weight, more preferably 0 to 30% by weight, particularly preferably 0 to 20% by weight of the detergent composition in terms of the cleaning performance.

The detergent composition of the present invention preferably contains the amino acid (I) in an amount of 0 to 50% by weight, more preferably 0 to 30% by weight, particularly preferably 0 to 20% by weight of the detergent composition in terms of the cleaning performance.

The detergent composition of the present invention preferably contains the other low-molecular-weight organic compounds (J) in an amount of 0 to 50% by weight, more preferably 0 to 30% by weight, particularly preferably 0 to 20% by weight of the detergent composition in terms of the cleaning performance.

The detergent composition of the present invention preferably contains the fatty acid (Q) in an amount of 0 to 50% by weight, more preferably 0 to 30% by weight, particularly preferably 0 to 20% by weight of the detergent composition in terms of the cleaning performance.

The detergent composition of the present invention preferably contains the oil/fat (N) in an amount of 0 to 50% by weight, more preferably 0 to 30% by weight, particularly preferably 0 to 20% by weight of the detergent composition in terms of the cleaning performance.

The detergent composition of the present invention preferably contains the protein (M) other than proteases in an amount of 0 to 50% by weight, more preferably 0 to 30% by weight, particularly preferably 0 to 20% by weight of the detergent composition in terms of the cleaning performance.

The detergent composition of the present invention can be produced by mixing these components, and any production method can be employed without limitation. The following describes one example.

(1) The surfactant (F), the solvent (E) and the other components are charged into a mixer provided with a stirrer and heating/cooling equipment in any order, and the mixture is stirred at 20 to 50° C. to be homogeneous.

(2) The proteinaceous protease inhibitor is added thereto and mixed at 20 to 50° C. for 30 minutes to 2 hours.

(3) The protease (D) is further added and stirred at 20 to 50° C. to provide a homogeneous mixture.

The detergent composition can be used for laundry detergents, automatic dishwashing detergents, contact lens detergents, and the like.

The detergent composition can be used in the same manner as conventional detergent compositions, and how to use the detergent composition is not limited at all. The following describes one example of usage as a laundry detergent.

(1) Tap water is charged into a washing machine with clothes, and a detergent composition is added at 25° C. and briefly stirred to dissolve.

(2) The clothes are washed in the washing machine.

(3) The liquid is drained out of the washing machine, and the clothes are rinsed with tap water once or twice.

(4) The clothes are optionally spin-dried.

EXAMPLES

The following examples and comparative examples are offered to illustrate the present invention in more detail, but should not be construed as limiting the present invention.

Preparation 1

A gene (SEQ ID NO:106) encoding the amino acid sequence of SEQ ID NO:1 (artificially synthesized product from Hokkaido System Science Co., Ltd. containing NcoI and BamHI restriction enzyme recognition sites at the 5' and 3' ends, respectively) was treated with NcoI and BamHI restriction enzymes, and ligated to the NcoI restriction enzyme site and the BamHI restriction enzyme site of a pET-22b plasmid (Novagen) to construct a plasmid (P1) expressing the protein of SEQ ID NO:1. Mutagenesis of the plasmid (P1) was carried out as described below using this plasmid and mutagenesis primers (SEQ ID NOs:42 and 43) for replacing glutamic acid at residue 12 with aspartic acid. Specifically, 0.5 µL (10 ng) of the plasmid (P1), 0.75 µL (7.5 pg) each of the mutagenesis primers (10 µM each), 2.5 µL of 10×PCR buffer (Takara Bio, Inc.), 2 µL of 2 mM deoxynucleotide triphosphoric acid (dNTP) mixture (Takara Bio, Inc.), 0.25 µL of DNA polymerase ExTaq (Takara Bio, Inc.) and 17 µL of deionized water were mixed, and PCR was performed with TaKaRa Thermal Cycler Dice (Takara Bio, Inc.). The reaction was performed by 30 cycles of heat denaturation at 94° C. for 2 minutes, at 98° C. for 10 seconds, at 50° C. for 10 seconds, and at 68° C. for 6.5 minutes. The PCR product was purified with QIAquick Gel Extraction Kit (Qiagen). To this (50 µL) were added 6 µL of 10× DpnI buffer and 3 µL of DpnI restriction enzyme (Takara Bio, Inc.), and the template was decomposed at 37° C. for 1 hour. A 5 µL portion of the resulting PCR product having been treated with the restriction enzyme was used to transform E. coli DH5α. Specifically, 5 µL of the PCR product having been treated with the restriction enzyme was added to 100 µL of E. Coli DH5α competent cells (TOYOBO), stored on ice for 30 minutes, and then heated at 42° C. for 90 seconds. To this was added 900 µL of SOC medium (TOYOBO), and the mixture was statically incubated at 37° C. for 1 hour. A 100 µL portion of the culture was inoculated into a LB/ampicillin plate, and incubated at 37° C. overnight. Colonies emerged and were picked into 1 mL of LB medium to be cultured for 12 hours. Then, Quantumprep Miniprep Kit (Bio-Rad) was used to purify a plasmid (P2) expressing the protein of SEQ ID NO:2 (100 µL). Analysis of the obtained plasmid by DNA sequence analysis service (Microgen Japan) confirmed that the plasmid contained the mutation.

Preparation 2

The same procedures were performed as in Preparation 1, except that mutagenesis primers (SEQ ID NOs:44 and 45) were used instead of the above mutagenesis primers (SEQ ID NOs:42 and 43). Thus, a plasmid (P3) expressing a protein having the amino acid sequence of SEQ ID NO:3 that differs from SEQ ID NO:1 by a substitution of alanine for glutamic acid at residue 12 was obtained.

Preparation 3

The same procedures were performed as in Preparation 1, except that mutagenesis primers (SEQ ID NOs:46 and 47) were used instead of the above mutagenesis primers (SEQ ID NOs:42 and 43). Thus, a plasmid (P4) expressing a protein having the amino acid sequence of SEQ ID NO:4 that differs from SEQ ID NO:1 by a substitution of alanine for valine at residue 38 was obtained.

Preparation 4

The same procedures were performed as in Preparation 1, except that mutagenesis primers (SEQ ID NOs:48 and 49) were used instead of the above mutagenesis primers (SEQ ID NOs:42 and 43). Thus, a plasmid (P5) expressing a protein having the amino acid sequence of SEQ ID NO:5 that differs from SEQ ID NO:1 by a substitution of leucine for valine at residue 38 was obtained.

Preparation 5

The same procedures were performed as in Preparation 1, except that mutagenesis primers (SEQ ID NOs:50 and 51) were used instead of the above mutagenesis primers (SEQ ID NOs:42 and 43). Thus, a plasmid (P6) expressing a protein having the amino acid sequence of SEQ ID NO:6 that differs from SEQ ID NO:1 by a substitution of isoleucine for valine at residue 38 was obtained.

Preparation 6

The same procedures were performed as in Preparation 1, except that mutagenesis primers (SEQ ID NOs:52 and 53) were used instead of the above mutagenesis primers (SEQ ID NOs:42 and 43). Thus, a plasmid (P7) expressing a protein having the amino acid sequence of SEQ ID NO:7 that differs from SEQ ID NO:1 by a substitution of alanine for methionine at residue 48 was obtained.

Preparation 7

The same procedures were performed as in Preparation 1, except that mutagenesis primers (SEQ ID NOs:54 and 55) were used instead of the above mutagenesis primers (SEQ ID NOs:42 and 43). Thus, a plasmid (P8) expressing a protein having the amino acid sequence of SEQ ID NO:8 that differs from SEQ ID NO:1 by a substitution of glycine for methionine at residue 48 was obtained.

Preparation 8

The same procedures were performed as in Preparation 1, except that mutagenesis primers (SEQ ID NOs:56 and 57) were used instead of the above mutagenesis primers (SEQ ID NOs:42 and 43). Thus, a plasmid (P9) expressing a protein having the amino acid sequence of SEQ ID NO:9 that differs from SEQ ID NO:1 by a substitution of alanine for tyrosine at residue 50 was obtained.

Preparation 9

The same procedures were performed as in Preparation 1, except that mutagenesis primers (SEQ ID NOs:58 and 59) were used instead of the above mutagenesis primers (SEQ ID NOs:42 and 43). Thus, a plasmid (P10) expressing a protein having the amino acid sequence of SEQ ID NO:10 that differs from SEQ ID NO:1 by a substitution of leucine for tyrosine at residue 50 was obtained.

Preparation 10

The same procedures were performed as in Preparation 1, except that mutagenesis primers (SEQ ID NOs:60 and 61) were used instead of the above mutagenesis primers (SEQ ID NOs:42 and 43). Thus, a plasmid (P11) expressing a protein having the amino acid sequence of SEQ ID NO:11 that differs from SEQ ID NO:1 by a substitution of phenylalanine for tyrosine at residue 50 was obtained.

Preparation 11

The same procedures were performed as in Preparation 1, except that mutagenesis primers (SEQ ID NOs:62 and 63) were used instead of the above mutagenesis primers (SEQ ID NOs:42 and 43). Thus, a plasmid (P12) expressing a protein having the amino acid sequence of SEQ ID NO:12 that differs from SEQ ID NO:1 by a substitution of alanine for arginine at residue 51 was obtained.

Preparation 12

The same procedures were performed as in Preparation 1, except that mutagenesis primers (SEQ ID NOs:64 and 65) were used instead of the above mutagenesis primers (SEQ ID NOs:42 and 43). Thus, a plasmid (P13) expressing a protein having the amino acid sequence of SEQ ID NO:13 that differs from SEQ ID NO:1 by a substitution of lysine for arginine at residue 51 was obtained.

Preparation 13

The same procedures were performed as in Preparation 1, except that mutagenesis primers (SEQ ID NOs:66 and 67) were used instead of the above mutagenesis primers (SEQ ID NOs:42 and 43). Thus, a plasmid (P14) expressing a protein having the amino acid sequence of SEQ ID NO:14 that differs from SEQ ID NO:1 by a substitution of histidine for arginine at residue 51 was obtained.

Preparation 14

The same procedures were performed as in Preparation 1, except that mutagenesis primers (SEQ ID NOs:68 and 69) were used instead of the above mutagenesis primers (SEQ ID NOs:42 and 43). Thus, a plasmid (P15) expressing a protein having the amino acid sequence of SEQ ID NO:15 that differs from SEQ ID NO:1 by a substitution of alanine for isoleucine at residue 52 was obtained.

Preparation 15

The same procedures were performed as in Preparation 1, except that mutagenesis primers (SEQ ID NOs:70 and 71)

were used instead of the above mutagenesis primers (SEQ ID NOs:42 and 43). Thus, a plasmid (P16) expressing a protein having the amino acid sequence of SEQ ID NO:16 that differs from SEQ ID NO:1 by a substitution of valine for isoleucine at residue 52 was obtained.

Preparation 16

The same procedures were performed as in Preparation 1, except that mutagenesis primers (SEQ ID NOs:72 and 73) were used instead of the above mutagenesis primers (SEQ ID NOs:42 and 43). Thus, a plasmid (P17) expressing a protein having the amino acid sequence of SEQ ID NO:17 that differs from SEQ ID NO:1 by a substitution of glutamic acid for aspartic acid at residue 53 was obtained.

Preparation 17

The same procedures were performed as in Preparation 1, except that mutagenesis primers (SEQ ID NOs:74 and 75) were used instead of the above mutagenesis primers (SEQ ID NOs:42 and 43). Thus, a plasmid (P18) expressing a protein having the amino acid sequence of SEQ ID NO:18 that differs from SEQ ID NO:1 by a substitution of alanine for aspartic acid at residue 53 was obtained.

Preparation 18

The same procedures were performed as in Preparation 1, except that mutagenesis primers (SEQ ID NOs:76 and 77) were used instead of the above mutagenesis primers (SEQ ID NOs:42 and 43). Thus, a plasmid (P19) expressing a protein having the amino acid sequence of SEQ ID NO:19 that differs from SEQ ID NO:1 by a substitution of alanine for arginine at residue 70 was obtained.

Preparation 19

The same procedures were performed as in Preparation 1, except that mutagenesis primers (SEQ ID NOs:78 and 79) were used instead of the above mutagenesis primers (SEQ ID NOs:42 and 43). Thus, a plasmid (P20) expressing a protein having the amino acid sequence of SEQ ID NO:20 that differs from SEQ ID NO:1 by a substitution of glycine for arginine at residue 70 was obtained.

Preparation 20

The same procedures were performed as in Preparation 1, except that mutagenesis primers (SEQ ID NOs:80 and 81) were used instead of the above mutagenesis primers (SEQ ID NOs:42 and 43). Thus, a plasmid (P21) expressing a protein having the amino acid sequence of SEQ ID NO:21 that differs from SEQ ID NO:1 by a substitution of lysine for arginine at residue 70 was obtained.

Preparation 21

Mutagenesis of the plasmid (P4) (containing alanine substituted for valine at residue 38) obtained in Preparation 3 was carried out as described below using the plasmid (P4) and mutagenesis primers (SEQ ID NOs:82 and 83) for replacing arginine at residue 51 and isoleucine at residue 52 with alanine. Specifically, 0.5 µL (10 ng) of the plasmid (P4), 0.75 µL (7.5 pg) each of the mutagenesis primers (10 µM each), 2.5 µL of 10×PCR buffer (Takara Bio, Inc.), 2 µL of 2 mM deoxynucleotide triphosphoric acid (dNTP) mixture (Takara Bio, Inc.), 0.25 µL of DNA polymerase ExTaq (Takara Bio, Inc.) and 17 µL of deionized water were mixed, and PCR was performed with TaKaRa Thermal Cycler Dice (Takara Bio, Inc.). The reaction was performed by 30 cycles of heat denaturation at 94° C. for 2 minutes, at 98° C. for 10 seconds, at 50° C. for 10 seconds, and at 68° C. for 6.5 minutes. The PCR product was purified with QIAquick Gel Extruction Kit (Qiagen). To this (50 µL) were added 6 µL of 10× DpnI buffer and 3 µL of DpnI restriction enzyme (Takara Bio, Inc.), and the template was decomposed at 37° C. for 1 hour.

A 5 µL portion of the resulting PCR product having been treated with the restriction enzyme was used to transform *E. coli* DH5α. Specifically, 5 µL of the PCR product having been treated with the restriction enzyme was added to 100 µL of *E. Coli* DH5α competent cells (TOYOBO), stored on ice for 30 minutes, and then heated at 42° C. for 90 seconds. To this was added 900 µL of SOC medium (TOYOBO), and the mixture was statically incubated at 37° C. for 1 hour. A 100 µL portion of the culture was inoculated into a LB/ampicillin plate, and incubated at 37° C. overnight. Colonies emerged and were picked into 1 mL of LB medium to be cultured for 12 hours. Then, Quantumprep Miniprep Kit (Bio-Rad) was used to purify a plasmid (P22) expressing the protein of SEQ ID NO:22 (100 µL). Analysis of the obtained plasmid by DNA sequence analysis service (Microgen Japan) confirmed that the plasmid contained the mutations.

Preparation 22

The same procedures were performed as in Preparation 21, except that mutagenesis primers (SEQ ID NOs:84 and 85) were used instead of the above mutagenesis primers (SEQ ID NOs:82 and 83). Thus, a plasmid (P23) expressing the protein of SEQ ID NO:23 that differs from SEQ ID NO:1 by substitutions of alanine for valine at residue 38, isoleucine at residue 52 and aspartic acid at residue 53 was obtained.

Preparation 23

The same procedures were performed as in Preparation 21, except that "the plasmid (P8) obtained in Preparation 7" was used instead of "the plasmid (P4) obtained in Preparation 3", and that "the mutagenesis primers (SEQ ID NOs:76 and 77)" were used instead of "the mutagenesis primers (SEQ ID NOs: 82 and 83)". Thus, a plasmid (P24) expressing the protein of SEQ ID NO:24 that differs from SEQ ID NO:1 by a substitution of glycine for methionine at residue 48 and a substitution of alanine for arginine at residue 70 was obtained.

Preparation 24

The same procedures were performed as in Preparation 23, except that "the plasmid (P4)" was used instead of "the plasmid (P8)". Thus, a plasmid (P25) expressing a protein having the amino acid sequence of SEQ ID NO:25 that differs from the SEQ ID NO:1 by substitutions of alanine for valine at residue 38 and arginine at residue 70 was obtained.

Preparation 25

A gene (SEQ ID NO:107) encoding the amino acid sequence of SEQ ID NO:26 (artificially synthesized product from Hokkaido System Science Co., Ltd. containing NcoI and BamHI restriction enzyme recognition sites at the 5' and 3' ends, respectively) was treated with NcoI and BamHI restriction enzymes, and ligated to the NcoI restriction enzyme site and the BamHI restriction enzyme site of a pET- 22b plasmid (Novagen) to construct a plasmid (P26) expressing the protein of SEQ ID NO:26 that differs from SEQ ID NO:1 by a substitution of aspartic acid for glutamic acid at residue 12, and substitutions of alanine for valine at residue 38, methionine at residue 48, tyrosine at residue 50, arginine at residue 51, isoleucine at residue 52, aspartic acid at residue 53, and arginine at residue 70.

Preparation 26

The same procedures were performed as in Preparation 1, except that the mutagenesis primers (SEQ ID NOs:86 and 87) were used instead of the mutagenesis primers (SEQ ID NOs: 42 and 43). Thus, a plasmid (P27) expressing a protein having the amino acid sequence of SEQ ID NO:27 that differs from SEQ ID NO:1 by a substitution of lysine for glutamic acid at residue 12 was obtained.

Preparation 27

The same procedures were performed as in Preparation 1, except that mutagenesis primers (SEQ ID NOs:88 and 89) were used instead of the above mutagenesis primers (SEQ ID NOs:42 and 43). Thus, a plasmid (P28) expressing a protein having the amino acid sequence of SEQ ID NO:28 that differs from SEQ ID NO:1 by a substitution of glycine for tyrosine at residue 50 was obtained.

Preparation 28

The same procedures were performed as in Preparation 1, except that mutagenesis primers (SEQ ID NOs:90 and 91) were used instead of the above mutagenesis primers (SEQ ID NOs:42 and 43). Thus, a plasmid (P29) expressing a protein having the amino acid sequence of SEQ ID NO:29 that differs from SEQ ID NO:1 by a substitution of asparagine for arginine at residue 70 was obtained.

Preparation 29

A gene (SEQ ID NO:108) encoding the amino acid sequence of SEQ ID NO:41 (artificially synthesized product from Hokkaido System Science Co., Ltd. containing NcoI and BamHI restriction enzyme recognition sites at the 5' and 3' ends, respectively) was treated with NcoI and BamHI restriction enzymes, and ligated to the NcoI restriction enzyme site and the BamHI restriction enzyme site of a pET-22b plasmid (Novagen) to construct a plasmid (P41) expressing the protein of SEQ ID NO:41. Mutagenesis of the plasmid (P41) was carried out as described below using this plasmid and mutagenesis primers (SEQ ID NOs:92 and 93) for replacing glutamic acid at residue 24 with alanine. Specifically, 0.5 µL (10 ng) of the plasmid (P41), 0.75 µL (7.5 pg) each of the mutagenesis primers (10 µM each), 2.5 µL of 10×PCR buffer (Takara Bio, Inc.), 2 µL of 2 mM deoxynucleotide triphosphoric acid (dNTP) mixture (Takara Bio, Inc.), 0.25 µL of DNA polymerase ExTaq (Takara Bio, Inc.) and 17 µL of deionized water were mixed, and PCR was performed with TaKaRa Thermal Cycler Dice (Takara Bio, Inc.). The reaction was performed by 30 cycles of heat denaturation at 94° C. for 2 minutes, at 98° C. for 10 seconds, at 50° C. for 10 seconds, and at 68° C. for 6.5 minutes. The PCR product was purified with QIAquick Gel Extruction Kit (Qiagen). To this (50 µL) were added 6 µL of 10× DpnI buffer and 3 µL of DpnI restriction enzyme (Takara Bio, Inc.), and the template was decomposed at 37° C. for 1 hour. A 5 µL portion of the resulting PCR product having been treated with the restriction enzyme was used to transform *E. coli* DH5α. Specifically, 5 µL of the PCR product having been treated with the restriction enzyme was added to 100 µL of *E. Coli* DH5α competent cells (TOYOBO), stored on ice for 30 minutes, and then heated at 42° C. for 90 seconds. To this was added 900 µL of SOC medium (TOYOBO), and the mixture was statically incubated at 37° C. for 1 hour. A 100 µL portion of the culture was inoculated into a LB/ampicillin plate, and incubated at 37° C. overnight. Colonies emerged and were picked into 1 mL of LB medium to be cultured for 12 hours. Then, Quantumprep Miniprep Kit (Bio-Rad) was used to purify a plasmid (P30) (100 µL) expressing the protein of SEQ ID NO:30 that has alanine at residue 24 which corresponds to residue 12 of the amino acid sequence (A), and has 90% homology to the inhibitor (B) of SEQ ID NO:3. Analysis of the obtained plasmid by DNA sequence analysis service (Microgen Japan) confirmed that the plasmid contained the mutation.

Preparation 30

The same procedures were performed as in Preparation 29, except that mutagenesis primers (SEQ ID NOs:94 and 95) were used instead of the above mutagenesis primers (SEQ ID NOs:92 and 93). Thus a plasmid (P31) expressing a protein having the amino acid sequence of SEQ ID NO:31 that differs from SEQ ID NO:41 by a substitution of alanine for isoleucine at residue 50 (which corresponds to residue 38 of SEQ ID NO:1) was obtained. This sequence has 90% homology to the inhibitor (B) of SEQ ID NO:4.

Preparation 31

The same procedures were performed as in Preparation 29, except that mutagenesis primers (SEQ ID NOs:96 and 97) were used instead of the above mutagenesis primers (SEQ ID NOs:92 and 93). Thus, a plasmid (P32) expressing a protein having the amino acid sequence of SEQ ID NO:32 that differs from SEQ ID NO:41 by a substitution of alanine for tyrosine at residue 62 (which corresponds to residue 50 of SEQ ID NO:1) was obtained. This sequence has 90% homology to the inhibitor (B) of SEQ ID NO:9.

Preparation 32

The same procedures were performed as in Preparation 29, except that mutagenesis primers (SEQ ID NOs:98 and 99) were used instead of the above mutagenesis primers (SEQ ID NOs:92 and 93). Thus, a plasmid (P33) expressing a protein having the amino acid sequence of SEQ ID NO:33 that differs from SEQ ID NO:41 by a substitution of alanine for arginine at residue 63 (which corresponds to residue 51 of SEQ ID NO:1) was obtained. This sequence has 90% homology to the inhibitor (B) of SEQ ID NO:12.

Preparation 33

The same procedures were performed as in Preparation 29, except that mutagenesis primers (SEQ ID NOs:100 and 101) were used instead of the above mutagenesis primers (SEQ ID NOs:92 and 93). Thus, a plasmid (P34) expressing a protein having the amino acid sequence of SEQ ID NO:34 that differs from SEQ ID NO:41 by a substitution of alanine for isoleucine at residue 64 (which corresponds to residue 52 of SEQ ID NO:1) was obtained. This sequence has 90% homology to the inhibitor (B) of SEQ ID NO:15.

Preparation 34

The same procedures were performed as in Preparation 29, except that mutagenesis primers (SEQ ID NOs:102 and 103)

were used instead of the above mutagenesis primers (SEQ ID NOs:92 and 93). Thus, a plasmid (P35) expressing a protein having the amino acid sequence of SEQ ID NO:35 that differs from SEQ ID NO:41 by a substitution of alanine for aspartic acid at residue 65 (which corresponds to residue 53 of SEQ ID NO:1) was obtained. This sequence has 90% homology to the inhibitor (B) of SEQ ID NO:18.

Preparation 35

The same procedures were performed as in Preparation 29, except that mutagenesis primers (SEQ ID NOs:104 and 105) were used instead of the mutagenesis primers (SEQ ID NOs: 92 and 93). Thus, a plasmid (P36) expressing a protein having the amino acid sequence of SEQ ID NO:36 that differs from SEQ ID NO:41 by a substitution of alanine for arginine at residue 82 (which corresponds to residue 70 of SEQ ID NO:1) was obtained. This sequence has 90% homology to the inhibitor (B) of SEQ ID NO:19.

sites at the 5' and 3' ends, artificially synthesized product from Hokkaido System Science Co., Ltd.) was treated with NcoI and BamHI restriction enzymes, and ligated to the NcoI restriction enzyme site and the BamHI restriction enzyme site of a pET-22b plasmid (Novagen) to construct a plasmid (P1) expressing the protein of SEQ ID NO:1.

Preparation 38

A gene (SEQ ID NO:108) encoding the amino acid sequence of SEQ ID NO:41 (artificially synthesized product from Hokkaido System Science Co., Ltd. containing NcoI and BamHI restriction enzyme recognition sites at the 5' and 3' ends, respectively) was treated with NcoI and BamHI restriction enzymes, and ligated to the NcoI restriction enzyme site and the BamHI restriction enzyme site of a pET-22b plasmid (Novagen) to construct a plasmid (P41) expressing the protein of SEQ ID NO:41 with 97% homology to SEQ ID NO:1. The amino acid sequence of SEQ ID NO:41 had, at

TABLE 1

| Position | SEQ ID NO | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Residue 12 | E | D | A | | | | | | | | | | | | | | | |
| Residue 38 | V | | | A | L | I | | | | | | | | | | | | |
| Residue 48 | M | | | | | | A | G | | | | | | | | | | |
| Residue 50 | Y | | | | | | | | A | L | F | | | | | | | |
| Residue 51 | R | | | | | | | | | | | A | K | H | | | | |
| Residue 52 | I | | | | | | | | | | | | | | A | V | | |
| Residue 53 | D | | | | | | | | | | | | | | | | E | A |
| Residue 70 | R | | | | | | | | | | | | | | | | | |

| Position | SEQ ID NO | | | | | | | | | | | | | | | | | |
|---|---|---|---|---|---|---|---|---|---|---|---|---|---|---|---|---|---|---|
| | 19 | 20 | 21 | 22 | 23 | 24 | 25 | 26 | 27 | 28 | 29 | 30 | 31 | 32 | 33 | 34 | 35 | 36 |
| Residue 12 | | | | | | | | D | K | | | A | | | | | | |
| Residue 38 | | | | A | A | | A | A | | | | | A | | | | | |
| Residue 48 | | | | | | G | | A | | | | | | | | | | |
| Residue 50 | | | | | | | | A | | G | | | | A | | | | |
| Residue 51 | | | | A | | | | A | | | | | | | A | | | |
| Residue 52 | | | | A | A | | | A | | | | | | | | A | | |
| Residue 53 | | | | | A | | | A | | | | | | | | | A | |
| Residue 70 | A | G | K | | | A | A | A | | | N | | | | | | | A |

Table 1 shows the positions of amino acids in SEQ ID NOs:2 to 28 which are substituted for corresponding amino acids in the amino acid sequence of SEQ ID NO:1, the positions, as expressed as corresponding positions in the amino acid sequence of SEQ ID NO:1, of amino acids in SEQ ID NO:29 to 36 which are substituted for corresponding amino acids in the amino acid sequence of SEQ ID NO:41, and the substituted amino acids.

Preparation 36

A gene (SEQ ID NO:109) encoding the amino acid sequence of SEQ ID NO:40 (artificially synthesized product from Hokkaido System Science Co., Ltd. containing NcoI and BamHI restriction enzyme recognition sites at the 5' and 3' ends, respectively) was treated with NcoI and BamHI restriction enzymes, and ligated to the NcoI restriction enzyme site and the BamHI restriction enzyme site of a pET-22b plasmid (Novagen) to construct a plasmid (P40) expressing the protein of SEQ ID NO:40.

Preparation 37

A gene encoding the amino acid sequence of SEQ ID NO:1 (containing NcoI and BamHI restriction enzyme recognition positions corresponding to residues 12, 38, 48, 50, 51, 52, 53, and 70 of SEQ ID NO:1, glutamic acid at residue 24 (which corresponds to residue 12 of SEQ ID NO:1), isoleucine at residue 50 (which corresponds to residue 38 of SEQ ID NO:1), methionine at residue 60 (which corresponds to residue 48 of SEQ ID NO:1), tyrosine at residue 62 (which corresponds to residue 50 of SEQ ID NO:1), arginine at residue 63 (which corresponds to residue 51 of SEQ ID NO:1), isoleucine at residue 64 (which corresponds to residue 52 of SEQ ID NO:1), aspartic acid at residue 65 (which corresponds to residue 53 of SEQ ID NO:1), and arginine at residue 82 (which corresponds to residue 70 of SEQ ID NO:1).

Examples 1 to 34

*E. Coli* BL21 (DE3) was transformed in the manner described above using the proteinaceous protease inhibitor expression plasmids (P2) to (P5) and (P7) to (P36) obtained in Preparations 1 to 4 and 6 to 35. The resulting proteinaceous protease inhibitor expressing strains were each inoculated into 1 mL of LB medium (containing 100 mg/L ampicillin), and cultured at 30° C. for 12 hours to give overnight cultures.

A 0.5 ml portion of each of the overnight cultures was inoculated into 5 ml of LB medium (containing 100 mg/L ampicillin), followed by shake culture at 30° C. for 3 hours. Thus, seven pre-cultures were obtained. All of the seven pre-cultures were each inoculated into 50 mL of a broth {containing 1.2 g of yeast extract (NIHON PHARMACEUTICAL CO., LTD.), 0.6 g of polypeptone (NIHON PHARMACEUTICAL CO., LTD.), 0.47 g of dipotassium phosphate, 0.11 g of monopotassium phosphate, 0.35 g of ammonium sulfate, 0.66 g of disodium phosphate dodecahydrate, 0.02 g of sodium citrate dihydrate, 0.2 g of glycerol, 1.5 g of lactalbumin hydrolysate, 0.3 g of an antifoamer ("KM-70" from Shin-Etsu Chemical Co., Ltd.), 1 mM magnesium sulfate, a trace metal solution (containing 18.9 µg of calcium chloride, 500 µg of iron (III) chloride, 9.0 µg of zinc sulfate heptahydrate, 5.1 µg of copper sulfate, 6.7 µg of manganese chloride tetrahydrate, 4.9 µg of cobalt chloride, and 200 µg of tetrasodium ethylenediaminetetraacetate) and 100 mg/L of ampicillin per 50 mL of water}, and incubated in a microorganism fermenter ("Bio Jr. 8" from ABLE Corporation) at a constant pH of 6.8 at a constant temperature of 30° C. Following the start of the incubation, 0.15 mL of a 1 M IPTG solution was added. At hour 14 from the start of the incubation, a glycerin/protein solution (containing 50% glycerin, 50 g/L of lactalbumin hydrolysate, 33 g/L of an antifoamer ("KM-70" from Shin-Etsu Chemical Co., Ltd.), and 100 mg/L of ampicillin) was dropwise added. At hour 48 from the start of the incubation, cultures (K-1) to (K-34) were collected.

The cultures (K-1) to (K-34) were separated using a His-tag purification carrier (Ni Sepharose 6 Fast Flow from GE Healthcare) to give proteinaceous protease inhibitor solutions (L-1) to (L-34). SDS-PAGE analysis of the solutions (L-1) to (L-34) confirmed that the proteinaceous protease inhibitor contents of the solutions (L-1) to (L-34) were all 1 g/L.

Comparative Examples 1 to 4

The same procedures were performed as in Example 1, except that "the plasmid (P1), (P40), (P41) and (P6)" were used instead of "the plasmid (P2)". Thus, proteinaceous protease inhibitor solutions (L'-1) to (L'-4) were obtained. The SDS-PAGE analysis revealed that the proteinaceous protease inhibitor contents of the solutions (L'-1) to (L'-4) were all 1 g/L.

The proteinaceous protease inhibitors obtained using the plasmid (P40) and the plasmid (P41) were analyzed for homology by the blastp algorithm of the homology search program "BLAST". The analysis revealed that their homologies to the proteinaceous protease inhibitor (B) of SEQ ID NO:25 were 65% and 89%.

Examples 35 to 68

Protein solutions (S-1) to (S-34) were prepared by mixing 350 µL each of the proteinaceous protease inhibitor solutions (L-1) to (L-34) obtained in Examples 1 to 34 with 350 µL of a 0.01% by weight alcalase solution (trade name: "Alcalase 2.5L", a dilution in a buffer containing 0.1 M Tris/HCl and 1 mM CaCl₂ (pH 8, 25° C.), available from Novozymes), and left standing for 20 minutes at 40° C.

Comparative Examples 5 to 8

Protein solutions (S'-1) to (S'-4) were prepared by mixing 350 µL each of the proteinaceous protease inhibitor solutions (L'-1) to (L'-4) obtained in Comparative Examples 1 to 4 with 350 µL of a 0.01% by weight alcalase solution (trade name: "Alcalase 2.5L", a dilution in a buffer containing 0.1 M Tris/HCl and 1 mM CaCl₂ (pH 8, 25° C.), available from Novozymes), and left standing for 20 minutes at 40° C.

TABLE 2

| | | SEQ ID NO | Protein solution | Immediately after preparation | | After three-month storage at 25° C. | | Retained protease activity (%) |
|---|---|---|---|---|---|---|---|---|
| | | | | Remaining activity (%) | Protease activity upon dilution (%) | Remaining activity (%) | Protease activity upon dilution (%) | |
| Example | 35 | 2 | (S-1) | 10 | 100 | 5 | 60 | 60 |
| | 36 | 3 | (S-2) | 7 | 89 | 5 | 60 | 67 |
| | 37 | 4 | (S-3) | 2 | 80 | 1 | 70 | 88 |
| | 38 | 5 | (S-4) | 11 | 100 | 2 | 35 | 35 |
| | 39 | 7 | (S-5) | 25 | 86 | 4 | 5 | 6 |
| | 40 | 8 | (S-6) | 23 | 85 | 6 | 6 | 7 |
| | 41 | 9 | (S-7) | 18 | 85 | 6 | 20 | 24 |
| | 42 | 10 | (S-8) | 9 | 90 | 5 | 60 | 67 |
| | 43 | 11 | (S-9) | 8 | 90 | 5 | 68 | 76 |
| | 44 | 12 | (S-10) | 2 | 20 | 2 | 19 | 95 |
| | 45 | 13 | (S-11) | 4 | 25 | 3 | 18 | 72 |
| | 46 | 14 | (S-12) | 5 | 85 | 3 | 70 | 82 |
| | 47 | 15 | (S-13) | 3 | 80 | 2 | 68 | 85 |
| | 48 | 16 | (S-14) | 9 | 95 | 1 | 68 | 72 |
| | 49 | 17 | (S-15) | 9 | 95 | 1 | 70 | 74 |
| | 50 | 18 | (S-16) | 3 | 85 | 1 | 74 | 87 |
| | 51 | 19 | (S-17) | 2 | 85 | 1 | 78 | 92 |
| | 52 | 20 | (S-18) | 10 | 100 | 2 | 60 | 60 |
| | 53 | 21 | (S-19) | 13 | 100 | 2 | 57 | 57 |
| | 54 | 22 | (S-20) | 1 | 82 | 1 | 80 | 98 |
| | 55 | 23 | (S-21) | 1 | 82 | 1 | 80 | 98 |
| | 56 | 24 | (S-22) | 20 | 82 | 1 | 11 | 13 |
| | 57 | 25 | (S-23) | 1 | 80 | 1 | 78 | 98 |
| | 58 | 26 | (S-24) | 19 | 85 | 2 | 10 | 12 |
| | 59 | 27 | (S-25) | 16 | 98 | 12 | 14 | 14 |
| | 60 | 28 | (S-26) | 18 | 90 | 10 | 15 | 17 |
| | 61 | 29 | (S-27) | 19 | 95 | 15 | 15 | 16 |
| | 62 | 30 | (S-28) | 15 | 80 | 5 | 18 | 23 |

TABLE 2-continued

|  |  | SEQ ID NO | Protein solution | Immediately after preparation | | After three-month storage at 25° C. | | |
|---|---|---|---|---|---|---|---|---|
|  |  |  |  | Remaining activity (%) | Protease activity upon dilution (%) | Remaining activity (%) | Protease activity upon dilution (%) | Retained protease activity (%) |
|  | 63 | 31 | (S-29) | 2 | 75 | 1 | 65 | 87 |
|  | 64 | 32 | (S-30) | 15 | 73 | 4 | 18 | 25 |
|  | 65 | 33 | (S-31) | 1 | 18 | 1 | 17 | 94 |
|  | 66 | 34 | (S-32) | 1 | 75 | 1 | 65 | 87 |
|  | 67 | 35 | (S-33) | 2 | 80 | 1 | 70 | 88 |
|  | 68 | 36 | (S-34) | 1 | 81 | 1 | 72 | 89 |
| Comparative | 5 | 1 | (S'-1) | 0 | 10 | 0 | 8 | 80 |
| Example | 6 | 40 | (S'-2) | 53 | 100 | 0 | 2 | 2 |
|  | 7 | 41 | (S'-3) | 0 | 8 | 0 | 6 | 75 |
|  | 8 | 6 | (S'-4) | 0 | 10 | 0 | 8 | 80 |

Measurement of Remaining Protease Activity of Protein Solutions Prepared Using Protein Solutions of Examples 35 to 68 and Comparative Examples 5 to 8, Immediately after Preparation Thereof —Measurement of Activity of Protein Solution (S)

From the respective protein solutions (S-1) to (S-34), (S'-1) and (S'-4) obtained in Examples 35 to 68 and Comparative Examples 5 to 8, 700 μL portions were sampled immediately after preparation of the solutions, and each combined with 70 μL of 50 mg/mL azocasein (dissolved in a buffer of 0.1M Tris/HCl and 1 mM $CaCl_2$ (pH 8, 25° C.), available from NACALAI TESQUE, INC.) to provide solutions (i) in which an enzyme reaction was initiated. From the respective solutions (i), 150 μL portions were sampled immediately after preparation thereof and every three minutes for three times, and each combined with 200 μL of 15% trichloriacetic acid solution. The mixtures were centrifuged at 15,000×g for 5 minutes, and the supernatants were each combined with 400 μL of 0.1 M NaOH, and measured for absorbance at 405 nm with a spectrophotometer. The change in the absorbance $\Delta A_\lambda$ ($\Delta A_\lambda = A_{\lambda,h} - A_{\lambda,0}$, wherein $A_{\lambda,0}$ is the absorbance measured immediately after preparation of a solution (i), and $A_{\lambda,h}$ is the absorbance measured at hour h after preparation of the solution (i)) was plotted along the vertical axis against the time h along the horizontal axis to determine the slope of a drawn line (coefficient $v_1$).

—Measurement of Activity of Blank Protein Solution

A solution free from proteinaceous protease inhibitors was prepared and measured for the absorbance in the manner described above to determine the slope of a drawn line (coefficient $v_1$).

A protein solution (T-1) was prepared by mixing 350 μL of a 0.01% by weight alcalase solution (trade name: "Alcalase 2.5L", a dilution in a buffer containing 0.1 M Tris/HCl and 1 mM $CaCl_2$ (pH 8, 25° C.), available from Novozymes) and 350 μL of a buffer {a buffer containing 0.1 M Tris/HCl and 1 mM $CaCl_2$ (pH 8, 25° C.)}, and left standing for 20 minutes at 40° C.

The same procedures were performed as in "Measurement of activity of protein solution (S)" to prepare a solution (ii), except that "the protein solution (T-1)" was used instead of "the protein solution (S-1)". The solution (ii) was measured for absorbance, and the change in the absorbance $\Delta A_\lambda$ ($\Delta A_\lambda = A_{\lambda,h} - A_{\lambda,0}$) was plotted along the vertical axis against the time h along the horizontal axis to determine the slope of a drawn line (coefficients $v_0$).

Table 2 shows the remaining protease activities of the protein solutions (S-1) to (S-34) and (S'-1) to (S'-4) calculated by the following formula (1).

Remaining activity (%)=$v_1/v_0 \times 100$ (1)

Measurement of Protease Activity Upon Dilution Immediately after Preparation

From the protein solutions (S-1) to (S-34) and (S'-1) to (S'-4) of Examples 35 to 68 and Comparative Examples 5 to 8, 10 μL portions were sampled immediately after preparation of the solutions, and each combined with 9990 μL of a buffer {a buffer containing 0.1 M Tris/HCl and 1 mM $CaCl_2$ (pH 8, 25° C.)}. Thus, diluted protein solutions (U-1) to (U-34) and (U'-1) to (U'-4) were obtained.

In order to measure the protease activity of the solutions upon dilution immediately after preparation thereof, the same procedures were performed as in "Measurement of activity of protein solution (S)", except that "the diluted protein solutions (U-1) to (U-34) and (U'-1) to (U'-4)" were used instead of "the protein solutions (S-1) to (S-34) and (S'-1) to (S'-4)", and samples were collected three times "every 30 minutes" instead of "every three minutes". Table 2 shows the results.

Measurement of Remaining Protease Activity after Three-Month Storage at 25° C.

The protein solutions (S-1) to (S-34) and (S'-1) to (S'-4) obtained in Examples 35 to 68 and Comparative Examples 5 to 8 were stored at 25° C. for three months.

In order to measure the remaining protease activity after three-month storage at 25° C., the same procedures were performed as in "Measurement of remaining protease activity immediately after preparation", except that "the protein solutions after three-month storage at 25° C." were measured instead of "the protein solutions immediately after preparation thereof". Table 2 shows the results.

Measurement of Protease Activity after Three-Month Storage at 25° C.

The same procedures were performed as in "Measurement of protease activity upon dilution immediately after preparation" to measure the protease activity of the protein solutions (S-1) to (S-34) and (S'-1) to (S'-4) obtained in Examples 35 to 68 and Comparative Examples 5 to 8 upon dilution after three-month storage at 25° C., except that "the protein solutions after three-month storage at 25° C." were measured instead of "the protein solutions immediately after preparation thereof". Table 2 shows the results.

Retained Protease Activity

The ratio between the protease activity immediately after preparation of a solution and the protease activity after three-month storage at 25° C. was determined for the respective protein solutions as retained protease activity by the following formula.

Retained protease activity (%)=(protease activity after three-month storage at 25° C.)/(protease activity immediately after preparation)×100

As seen in the evaluation results shown in Table 2, the protein solutions of Comparative Examples 5 and 8 containing the proteinaceous protease inhibitor of SEQ ID NO:1 or 6 showed a remaining activity of 0% immediately after preparation of the solutions, but showed a protease activity upon dilution as low as 10%. This indicates that their protein activity is inhibited but cannot be restored. Likewise, the protein solution of Comparative Example 7 containing the proteinaceous protease inhibitor of SEQ ID NO:41, which has 97% homology to the amino acid sequence (A), and does not satisfy any of the conditions (1) to (8) of the present invention, showed a protease activity upon dilution as low as 8%. This indicates that its protease activity cannot be restored.

The protein solution of Comparative Example 6, the proteinaceous protease inhibitor of which has 65% homology to a proteinaceous protease inhibitor of the present invention, showed a retained protease activity as low as 2%. This indicates that its protease activity declines during three-month storage.

By contrast, compared to the protein solution of Comparative Example 6 containing the proteinaceous protease inhibitor of SEQ ID NO:40 which has 65% homology to a proteinaceous protease inhibitor of the present invention, the protein solutions of Examples 35 to 68 containing the proteinaceous protease inhibitors of the present invention showed a lower remaining activity, and therefore were found to be able to inhibit the protease activity better when these inhibitors are used at the same concentration. The protease activities upon dilution immediately after preparation of the protein solution Examples 35 to 68 were all not lower than 18%. This indicates that when these solutions are diluted, the inhibited protease activity can be efficiently restored.

The protein solutions of Examples 35 to 68 containing the proteinaceous protease inhibitors of the present invention showed a protease activity measured after three-month storage at 25° C. of 5% or higher, and a retained protease activity of 6 to 98%. This indicates that these solutions can retain certain levels of protease activity even after three-month storage.

Examples 69 to 102

The proteinaceous protease inhibitor solutions (L-1) to (L-34), the protease (D), the surfactant (F), the protein (M) other than proteases, the chelating agent and the solvent (E) were mixed in amounts shown in Tables 3 to 5 at 25° C. to provide detergent compositions of Examples 69 to 102.

Comparative Examples 9 to 12

The proteinaceous protease inhibitor solutions (L'-1) to (L'-4), the protease (D), the surfactant (F), the protein (M) other than proteases, the chelating agent and the solvent (E) were mixed in amounts shown in Table 5 at 25° C. to provide detergent compositions of Comparative Examples 9 to 12.

TABLE 3

| | | | Example | | | | | | | | | | | | |
|---|---|---|---|---|---|---|---|---|---|---|---|---|---|---|---|
| | | | 69 | 70 | 71 | 72 | 73 | 74 | 75 | 76 | 77 | 78 | 79 | 80 |
| Liquid detergent composition (parts by weight) | Protease (D) | Alcalase aqueous solution | 1 | 1 | 1 | 1 | 1 | 1 | 1 | 1 | 1 | 1 | 1 | 1 |
| | Proteinaceous protease inhibitor solution | (L-1) | 1 | | | | | | | | | | | |
| | | (L-2) | | 1 | | | | | | | | | | |
| | | (L-3) | | | 1 | | | | | | | | | |
| | | (L-4) | | | | 1 | | | | | | | | |
| | | (L-5) | | | | | 1 | | | | | | | |
| | | (L-6) | | | | | | 1 | | | | | | |
| | | (L-7) | | | | | | | 1 | | | | | |
| | | (L-8) | | | | | | | | 1 | | | | |
| | | (L-9) | | | | | | | | | 1 | | | |
| | | (L-10) | | | | | | | | | | 1 | | |
| | | (L-11) | | | | | | | | | | | 1 | |
| | | (L-12) | | | | | | | | | | | | 1 |
| | Surfactant (F) | 11 mole EO adduct of oleylalcohol | 20 | 20 | 20 | 20 | 20 | 20 | 20 | 20 | 20 | 20 | 20 | 20 |
| | | Sodium/monoethanolamine dodecylbenzene sulfonate | 15 | 15 | 15 | 15 | 15 | 15 | 15 | 15 | 15 | 15 | 15 | 15 |
| | Protein (M) other than protease | Endolase aqueous solution | 1.2 | 1.2 | 1.2 | 1.2 | 1.2 | 1.2 | 1.2 | 1.2 | 1.2 | 1.2 | 1.2 | 1.2 |
| | Chelating agent | Citric acid | 0.1 | 0.1 | 0.1 | 0.1 | 0.1 | 0.1 | 0.1 | 0.1 | 0.1 | 0.1 | 0.1 | 0.1 |
| | Solvent (E) | Tap water | 61.7 | 61.7 | 61.7 | 61.7 | 61.7 | 61.7 | 61.7 | 61.7 | 61.7 | 61.7 | 61.7 | 61.7 |
| | Total | | 100 | 100 | 100 | 100 | 100 | 100 | 100 | 100 | 100 | 100 | 100 | 100 |
| Evaluation result | | Wash removability immediately after preparation (%) | 69.0 | 67.9 | 67.0 | 69.0 | 67.6 | 67.5 | 67.5 | 68.0 | 68.0 | 46.2 | 48.5 | 67.5 |
| | | Wash removability after two-month storage (%) | 62.3 | 46.2 | 64.7 | 53.1 | 39.3 | 39.8 | 46.2 | 62.3 | 64.2 | 45.7 | 45.3 | 64.7 |
| | | Retained cleaning performance (%) | 90.3 | 68.0 | 96.5 | 77.0 | 58.1 | 58.9 | 68.4 | 91.7 | 94.4 | 99.0 | 93.4 | 95.8 |

TABLE 4

| | | | Example | | | | | | | | | | | | | |
|---|---|---|---|---|---|---|---|---|---|---|---|---|---|---|---|---|
| | | | 81 | 82 | 83 | 84 | 85 | 86 | 87 | 88 | 89 | 90 | 91 | 92 | 93 |
| Liquid detergent composition (parts by weight) | Protease (D) | Alcalase aqueous solution | 1 | 1 | 1 | 1 | 1 | 1 | 1 | 1 | 1 | 1 | 1 | 1 | 1 |
| | Proteinaceous protease inhibitor solution | (L-13) | 1 | | | | | | | | | | | | |
| | | (L-14) | | 1 | | | | | | | | | | | |
| | | (L-15) | | | 1 | | | | | | | | | | |
| | | (L-16) | | | | 1 | | | | | | | | | |
| | | (L-17) | | | | | 1 | | | | | | | | |
| | | (L-18) | | | | | | 1 | | | | | | | |
| | | (L-19) | | | | | | | 1 | | | | | | |
| | | (L-20) | | | | | | | | 1 | | | | | |
| | | (L-21) | | | | | | | | | 1 | | | | |
| | | (L-22) | | | | | | | | | | 1 | | | |
| | | (L-23) | | | | | | | | | | | 1 | | |
| | | (L-24) | | | | | | | | | | | | 1 | |
| | | (L-25) | | | | | | | | | | | | | 1 |
| | Surfactant (F) | 11 mole EO adduct of oleylalcohol | 20 | 20 | 20 | 20 | 20 | 20 | 20 | 20 | 20 | 20 | 20 | 20 | 20 |
| | | Sodium/monoethanolamine dodecylbenzene sulfonate | 15 | 15 | 15 | 15 | 15 | 15 | 15 | 15 | 15 | 15 | 15 | 15 | 15 |
| | Protein (M) other than protease | Endolase aqueous solution | 1.2 | 1.2 | 1.2 | 1.2 | 1.2 | 1.2 | 1.2 | 1.2 | 1.2 | 1.2 | 1.2 | 1.2 | 1.2 |
| | Chelating agent | Citric acid | 0.1 | 0.1 | 0.1 | 0.1 | 0.1 | 0.1 | 0.1 | 0.1 | 0.1 | 0.1 | 0.1 | 0.1 | 0.1 |
| | Solvent (E) | Tap water | 61.7 | 61.7 | 61.7 | 61.7 | 61.7 | 61.7 | 61.7 | 61.7 | 61.7 | 61.7 | 61.7 | 61.7 | 61.7 |
| | Total | | 100 | 100 | 100 | 100 | 100 | 100 | 100 | 100 | 100 | 100 | 100 | 100 | 100 |
| Evaluation result | Wash removability immediately after preparation (%) | | 67.0 | 68.5 | 68.5 | 67.5 | 67.5 | 69.0 | 69.0 | 67.2 | 67.2 | 67.2 | 67.0 | 67.5 | 68.8 |
| | Wash removability after two-month storage (%) | | 64.2 | 64.2 | 64.7 | 65.6 | 66.5 | 62.3 | 61.6 | 67.0 | 67.0 | 42.1 | 66.5 | 41.6 | 43.4 |
| | Retained cleaning performance (%) | | 95.8 | 93.7 | 94.4 | 97.2 | 98.6 | 90.3 | 89.3 | 99.7 | 99.7 | 62.6 | 99.3 | 61.6 | 63.1 |

TABLE 5

| | | | Example | | | | | | | | | Comparative Example | | | |
|---|---|---|---|---|---|---|---|---|---|---|---|---|---|---|---|
| | | | 94 | 95 | 96 | 97 | 98 | 99 | 100 | 101 | 102 | 9 | 10 | 11 | 12 |
| Liquid detergent composition (parts by weight) | Protease (D) | Alcalase aqueous solution | 1 | 1 | 1 | 1 | 1 | 1 | 1 | 1 | 1 | 1 | 1 | 1 | 1 |
| | Proteinaceous protease inhibitor solution | (L-26) | 1 | | | | | | | | | | | | |
| | | (L-27) | | 1 | | | | | | | | | | | |
| | | (L-28) | | | 1 | | | | | | | | | | |
| | | (L-29) | | | | 1 | | | | | | | | | |
| | | (L-30) | | | | | 1 | | | | | | | | |
| | | (L-31) | | | | | | 1 | | | | | | | |
| | | (L-32) | | | | | | | 1 | | | | | | |
| | | (L-33) | | | | | | | | 1 | | | | | |
| | | (L-34) | | | | | | | | | 1 | | | | |
| | | (L'-1) | | | | | | | | | | 1 | | | |
| | | (L'-2) | | | | | | | | | | | 1 | | |
| | | (L'-3) | | | | | | | | | | | | 1 | |
| | | (L'-4) | | | | | | | | | | | | | 1 |
| | Surfactant (F) | 11 mole EO adduct of oleylalcohol | 20 | 20 | 20 | 20 | 20 | 20 | 20 | 20 | 20 | 20 | 20 | 20 | 20 |
| | | Sodium/monoethanolamine dodecylbenzene sulfonate | 15 | 15 | 15 | 15 | 15 | 15 | 15 | 15 | 15 | 15 | 15 | 15 | 15 |
| | Protein (M) other than protease | Endolase aqueous solution | 1.2 | 1.2 | 1.2 | 1.2 | 1.2 | 1.2 | 1.2 | 1.2 | 1.2 | 1.2 | 1.2 | 1.2 | 1.2 |
| | Chelating agent | Citric acid | 0.1 | 0.1 | 0.1 | 0.1 | 0.1 | 0.1 | 0.1 | 0.1 | 0.1 | 0.1 | 0.1 | 0.1 | 0.1 |
| | Solvent (E) | Tap water | 61.7 | 61.7 | 61.7 | 61.7 | 61.7 | 61.7 | 61.7 | 61.7 | 61.7 | 61.7 | 61.7 | 61.7 | 61.7 |
| | Total | | 100 | 100 | 100 | 100 | 100 | 100 | 100 | 100 | 100 | 100 | 100 | 100 | 100 |
| Evaluation result | Wash removability immediately after preparation (%) | | 68.0 | 68.5 | 67.0 | 65.8 | 65.4 | 45.3 | 65.8 | 67.0 | 67.1 | 41.6 | 69.0 | 40.7 | 41.6 |

TABLE 5-continued

|  | | Example | | | | | | | | | Comparative Example | | | |
|---|---|---|---|---|---|---|---|---|---|---|---|---|---|---|
|  | | 94 | 95 | 96 | 97 | 98 | 99 | 100 | 101 | 102 | 9 | 10 | 11 | 12 |
| Wash removability after two-month storage (%) | | 43.9 | 43.9 | 45.3 | 63.5 | 45.3 | 44.8 | 63.5 | 64.7 | 65.1 | 40.7 | 37.9 | 39.8 | 40.7 |
| Retained cleaning performance (%) | | 64.6 | 64.1 | 67.6 | 96.5 | 69.3 | 99.0 | 96.5 | 96.5 | 97.1 | 97.8 | 55.0 | 97.7 | 97.8 |

The amounts of the components shown in Tables 3 to 5 were all parts by weight. The protease (D) shown in Tables 3 to 5 was the following protease.

Alcalase aqueous solution (alcalase content estimated by SDS-PAGE: 0.1 g/mL): trade name "Alcalase 2.5L" from Novozymes The protein (M) other than proteases shown in Tables 3 to 5 was the following protein.

Cellulase aqueous solution (cellulase content estimated by SDS-PAGE: 0.01 g/mL): trade name "Endolase" from Novozymes The detergent compositions obtained in Examples 69 to 102 and Comparative Examples 9 to 12 were analyzed by the following cleaning performance test.

Cleaning Performance Test

Wash Removability Immediately after Preparation

A 0.8 g portion of each of the detergent compositions obtained in Examples 69 to 102 and Comparative Examples 9 to 12 was dissolved in 999.2 g of water immediately after preparation of the detergent compositions. In each of the obtained solutions, five artificially soiled wet cloths (4 cm×4 cm) were immersed, and then washed and rinsed using a tergotometer (Daieikagaku Co., Ltd.) under the following conditions. The cloths were then taken out and dried in a geer oven (GPS-222 from TABAI) at 70° C. for 60 minutes. Thus, test cloths were prepared. Each of the test cloths was measured for reflectance at 540 nm at two points on each surface (four points for each cloth, 20 points for each set of five cloths) using a multi-light source spectrophotometer colorimeter (Suga Test Instruments Co., Ltd.). The results were averaged, and the average was used to calculate the wash removability (%) by the following formula. Tables 3 to 5 show the results.

(Washing Condition)

Duration: 10 minutes, temperature: 25° C., revolution: 120 rpm (Rinsing Condition)

Duration: 1 minute, temperature: 25° C., revolution: 120 rpm (Wash Removability)

Wash removability (%) = $\{(R_W - R_S)/(R_I - R_S)\} \times 100$

In the formula, $R_I$ is the reflectance of clean cloths, $R_W$ is the reflectance of washed cloths, and $R_S$ is the reflectance of soiled cloths.

The artificially soiled wet cloths used were artificially soiled wet cloths from Sentaku Kagaku Kyoukai (Foundation for Laundry Science) (reflectance at 540 nm: 40±5%). Their soil composition is shown in Table 6.

TABLE 6

|  |  |  | Parts by weight |
|---|---|---|---|
| Organic Component | Oil/fat | Oleic acid | 14.2 |
|  |  | Triolein | 7.8 |
|  |  | Cholesteryl oleate | 6.1 |
|  |  | Liquid paraffin | 1.3 |
|  |  | Squalene | 1.3 |
|  |  | Cholesterol | 0.8 |
|  | Protein | Gelatin | 3.5 |
| Inorganic component |  | Carbon black | 2.5 |
|  |  | Red yellow soil | 20 |

Wash Removability after Three-Month Storage at 25° C.

The same washing test as that performed in <Wash removability immediately after preparation> was performed using the detergent compositions of Examples 69 to 102 and Comparative Examples 9 to 12 to determine wash removability, except that the detergent compositions were subjected to the test not immediately after preparation thereof but after three-month storage at 25° C. Tables 3 to 5 show the results.

Retained Cleaning Performance

The ratio between the wash removability immediately after preparation and the wash removability after three-month storage at 25° C. were calculated as the retained cleaning performance by the following formula.

Retained cleaning performance(%) = (wash removability after three-month storage at 25° C.)/(wash removability immediately after preparation)×100

As seen from the results shown in Tables 3 to 5, the detergent compositions of the present invention show high retained cleaning performance and thus are able to retain cleaning performance for a long time.

INDUSTRIAL APPLICABILITY

Because of its ability to efficiently inhibit the activity of proteases for a long time, the proteinaceous protease inhibitor of the present invention is useful in fields of, for example, medical products, food products, detergents, and biochemistry. The protein solution of the present invention can retain protease activity for a long time because the activity of the protease therein is sufficiently inhibited. Accordingly, the protein solution of the present invention is useful in fields of, for example, medical products, food products, detergents, and biochemistry. Specifically, it can be used, for example, in liquid medical protein preparations, liquid enzyme preparations, industrial enzyme aqueous solutions, liquid detergents, beverage, measuring reagents for diagnostic agents, and protein standard solutions. The detergent composition of the present invention can retain cleaning performance for a long time because the activity of the protease therein is sufficiently inhibited. Accordingly, the detergent composition of the present invention can be used for laundry detergents, automatic dishwashing detergents and contact lens detergents, in particular, for liquid laundry detergents.

The invention claimed is:

1. A proteinaceous protease inhibitor comprising an amino acid sequence (Y) or an amino acid sequence (Y'), the amino acid sequence (Y) being different from the amino acid sequence (A) of a proteinaceous protease inhibitor (BC), represented by SEQ ID NO: 1, by one to eight amino acid replacements, the amino acid sequence (Y') having at least 80% homology to the amino acid sequence (Y), wherein the proteinaceous protease inhibitor satisfies that the amino acid residue at a position corresponding to residue 38 of the amino acid sequence (A) in the amino acid sequence (Y) or (Y') is Ala, Gly, Leu, Phe, Ser, Thr or Trp.

2. A proteinaceous protease inhibitor comprising an amino acid sequence (Y) or an amino acid sequence (Y'), the amino acid sequence (Y) being different from the amino acid sequence (A) of a proteinaceous protease inhibitor (BC), represented by SEQ ID NO: 1, by one to eight amino acid replacements, the amino acid sequence (Y') having at least 80% homology to the amino acid sequence (Y), wherein the proteinaceous protease inhibitor satisfies that the amino acid residue at a position corresponding to residue 52 of the amino acid sequence (A) in the amino acid sequence (Y) or (Y') is Glu, Ala, Asn, Gln, Leu, Ser, Thr or Val.

3. A proteinaceous protease inhibitor comprising an amino acid sequence (Y) or an amino acid sequence (Y'), the amino acid sequence (Y) being different from the amino acid sequence (A) of a proteinaceous protease inhibitor (BC), represented by SEQ ID NO: 1, by one to eight amino acid replacements, the amino acid sequence (Y') having at least 80% homology to the amino acid sequence (Y), wherein the proteinaceous protease inhibitor satisfies that the amino acid residue at a position corresponding to residue 53 of the amino acid sequence (A) in the amino acid sequence (Y) or (Y') is Glu, Ala, Asn, Gln, Ile, Leu, Ser, Thr or Val.

4. A protein solution comprising:
   a proteinaceous protease inhibitor according to claim 1;
   a protease (D); and
   a solvent (E).

5. A detergent composition comprising:
   a proteinaceous protease inhibitor according to claim 1;
   a protease (D);
   a solvent (E); and
   a surfactant (F).

6. A protein solution comprising:
   a proteinaceous protease inhibitor according to claim 2;
   a protease (D); and
   a solvent (E).

7. A detergent composition comprising:
   a proteinaceous protease inhibitor according to claim 2;
   a protease (D);
   a solvent (E); and
   a surfactant (F).

8. A protein solution comprising:
   a proteinaceous protease inhibitor according to claim 3;
   a protease (D); and
   a solvent (E).

9. A detergent composition comprising:
   a proteinaceous protease inhibitor according to claim 3;
   a protease (D);
   a solvent (E); and
   a surfactant (F).

10. The proteinaceous protease inhibitor according to claim 1, wherein the proteinaceous protease inhibitor satisfies at least one of the following conditions (1) and (3) to (8):
    (1) the amino acid residue at a position corresponding to residue 12 of the amino acid sequence (A) in the amino acid sequence (Y) or (Y') is an amino acid (X1) defined below;
    (3) the amino acid residue at a position corresponding to residue 48 of the amino acid sequence (A) in the amino acid sequence (Y) or (Y') is an amino acid (X3) defined below;
    (4) the amino acid residue at a position corresponding to residue 50 of the amino acid sequence (A) in the amino acids (Y) or (Y') is an amino acid (X4) defined below;
    (5) the amino acid residue at a position corresponding to residue 51 of the amino acid (A) in the amino acid (Y) or (Y') is an amino acid (X5) defined below;
    (6) the amino acid residue at a position corresponding to residue 52 of the amino acid (A) in the amino acid (Y) or (Y') is an amino acid (X6) defined below;
    (7) the amino acid residue at a position corresponding to residue 53 of the amino acid sequence (A) in the amino acid sequence (Y) or (Y') is an amino acid (X7) defined below;
    (8) the amino acid residue at a position corresponding to residue 70 of the amino acid sequence (A) in the amino acid sequence (Y) or (Y') is an amino acid (X8) defined below:
    (X1): any of amino acids (X0) other than Glu
    (X3): any of the amino acids (X0) other than Met
    (X4): any of the amino acids (X0) other than Tyr
    (X5): any of the amino acids (X0) other than Arg
    (X6): any of the amino acids (X0) other than Ile
    (X7): any of the amino acids (X0) other than Asp
    (X8): any of the amino acids (X0) other than Arg; and
    (X0): Ala, Arg, Asn, Asp, Cys, Gly, Gln, Glu, His, Ile, Leu, Lys, Met, Phe, Pro, Ser, Thr, Trp, Tyr, or Val.

11. The proteinaceous protease inhibitor according to claim 10,
    wherein the amino acid (X1) is Asp, Ala, Asn, Gln, Leu, Lys, Ser, Thr or Val.

12. The proteinaceous protease inhibitor according to claim 10,
    wherein the amino acid (X3) is Ala, Ile, Leu, Ser, Thr, Gly or Val.

13. The proteinaceous protease inhibitor according to claim 10,
    wherein the amino acid (X4) is Ala, Phe, Gly, Ile, Leu, Ser, Thr or Val.

14. The proteinaceous protease inhibitor according to claim 10,
    wherein amino acid (X5) is Ala, Lys, His, Ile, Leu, Ser, Thr or Val.

15. The proteinaceous protease inhibitor according to claim 10,
    wherein the amino acid (X6) is Glu, Ala, Asn, Gln, Leu, Ser, Thr or Val.

16. The proteinaceous protease inhibitor according to claim 10,
    wherein the amino acid (X7) is Glu, Ala, Asn, Gln, Ile, Leu, Ser, Thr or Val.

17. The proteinaceous protease inhibitor according to claim 10,
    wherein the amino acid (X8) is Ala, Asn, Lys, His, Ile, Leu, Ser, Gly, Thr or Val.

18. The proteinaceous protease inhibitor according to claim 2,
    wherein the proteinaceous protease inhibitor satisfies at least one of the following conditions (1) to (5), (7) and (8):
    (1) the amino acid residue at a position corresponding to residue 12 of the amino acid sequence (A) in the amino acid sequence (Y) or (Y') is an amino acid (X1) defined below;
    (2) the amino acid residue at a position corresponding to residue 38 of the amino acid sequence (A) in the amino acid sequence (Y) or (Y') is an amino acid (X2) defined below;
    (3) the amino acid residue at a position corresponding to residue 48 of the amino acid sequence (A) in the amino acid sequence (Y) or (Y') is an amino acid (X3) defined below;
    (4) the amino acid residue at a position corresponding to residue 50 of the amino acid sequence (A) in the amino acid sequence (Y) or (Y') is an amino acid (X4) defined below;

(5) the amino acid residue at a position corresponding to residue 51 of the amino acid sequence (A) in the amino acid sequence (Y) or (Y') is an amino acid (X5) defined below;
(7) the amino acid residue at a position corresponding to residue 53 of the amino acid sequence (A) in the amino acid sequence (Y) or (Y') is an amino acid (X7) defined below;
(8) the amino acid residue at a position corresponding to residue 70 of the amino acid sequence (A) in the amino acid sequence (Y) or (Y') is an amino acid (X8) defined below:
(X1): any of amino acids (X0) other than Glu
(X2): any of the amino acids (X0) other than Val and Ile
(X3): any of the amino acids (X0) other than Met
(X4): any of the amino acids (X0) other than Tyr
(X5): any of the amino acids (X0) other than Arg
(X7): any of the amino acids (X0) other than Asp
(X8): any of the amino acids (X0) other than Arg; and
(X0): Ala, Arg, Asn, Asp, Cys, Gly, Gln, Glu, His, Ile, Leu, Lys, Met, Phe, Pro, Ser, Thr, Trp, Tyr, or Val.

19. The proteinaceous protease inhibitor according to claim 18,
wherein the amino acid (X5) is Ala, Lys, His, Ile, Leu, Ser, Thr or Val.

20. The proteinaceous protease inhibitor according to claim 18,
wherein the amino acid (X7) is Glu, Ala, Asn, Gln, Ile, Leu, Ser, Thr or Val.

21. The proteinaceous protease inhibitor according to claim 3,
wherein the proteinaceous protease inhibitor satisfies at least one of the following conditions (1) to (6) and (8):
(1) the amino acid residue at a position corresponding to residue 12 of the amino acid sequence (A) in the amino acid sequence (Y) or (Y') is an amino acid (X1) defined below;
(2) the amino acid residue at a position corresponding to residue 38 of the amino acid sequence (A) in the amino acid sequence (Y) or (Y') is an amino acid (X2) defined below;
(3) the amino acid residue at a position corresponding to residue 48 of the amino acid sequence (A) in the amino acid sequence (Y) or (Y') is an amino acid (X3) defined below;
(4) the amino acid residue at a position corresponding to residue 50 of the amino acid sequence (A) in the amino acid sequence (Y) or (Y') is an amino acid (X4) defined below;
(5) the amino acid residue at a position corresponding to residue 51 of the amino acid sequence (A) in the amino acid sequence (Y) or (Y') is an amino acid (X5) defined below;
(6) the amino acid residue at a position corresponding to residue 52 of the amino acid sequence (A) in the amino acid sequence (Y) or (Y') is an amino acid (X6) defined below;
(8) the amino acid residue at a position corresponding to residue 70 of the amino acid sequence (A) in the amino acid sequence (Y) or (Y') is an amino acid (X8) defined below:
(X1): any of amino acids (X0) other than Glu
(X2): any of the amino acids (X0) other than Val and Ile
(X3): any of the amino acids (X0) other than Met
(X4): any of the amino acids (X0) other than Tyr
(X5): any of the amino acids (X0) other than Arg
(X6): any of the amino acids (X0) other than Ile
(X8): any of the amino acids (X0) other than Arg; and
(X0): Ala, Arg, Asn, Asp, Cys, Gly, Gln, Glu, His, Ile, Leu, Lys, Met, Phe, Pro, Ser, Thr, Trp, Tyr, or Val.

22. The proteinaceous protease inhibitor according to claim 21,
wherein the amino acid (X5) is Ala, Lys, His, Ile, Leu, Ser, Thr or Val.

* * * * *